(12) United States Patent
Sabatucci et al.

(10) Patent No.: US 6,933,322 B2
(45) Date of Patent: Aug. 23, 2005

(54) SUBSTITUTED NAPHTHYLENES FOR THE TREATMENT OF NON-INSULIN DEPENDENT DIABETES MELLITUS

(75) Inventors: Joseph P. Sabatucci, Collegeville, PA (US); Craig E. Caufield, New York, NY (US); Alexander A. Greenfield, Princeton Junction, NJ (US); Schuyler Antane, Lawrenceville, NJ (US); Eamonn P. Morrison, Yardley, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/408,877

(22) Filed: Apr. 8, 2003

(65) Prior Publication Data

US 2003/0216442 A1 Nov. 20, 2003

Related U.S. Application Data

(60) Provisional application No. 60/371,373, filed on Apr. 10, 2002.

(51) Int. Cl.⁷ .................. A61K 31/085; C07C 211/44
(52) U.S. Cl. ........................ 514/717; 568/585
(58) Field of Search .................. 514/717; 568/585

(56) References Cited

PUBLICATIONS

Mosmann, Journal of Immunological Methods, 65, 55–63 (1983).
Goodman, Michael, Biochem. J., 150, 137–139 (1975).
Lowry, et al., J. Biol. Chem., 193, 265–275 (1951).
Jomain–Baum et al., The Journal of Biological Chemistry, 251(1), 37–44 (1976).
Consoli, et al., Diabetes, 38, 550–557 (1989).
Chang et al., Diabetes, 32, 830–838 (1983).
Brichard, et al., Diabetes, 39, 1326–1332 (1990).
O'Brien, et al., Diabetes Care, 13(3), 327–339 (1990).
Coleman, Diabetologia, 14, 141–148 (1978).
Heding, Diabetologia, 8, 260–266 (1972).
Smith et al., Analytical Biochemistry, 150, 76–85 (1985).
Hardman et al., Methods in Enzymology, vol. XXXIX, Part D, 25–36 (1975).
Vranckx, et al., Biochemistry and Molecular Biology, vol. 65, 55–63 (1983).

*Primary Examiner*—Taofiq Solola
(74) *Attorney, Agent, or Firm*—Fish & Richardson P.C.

(57) ABSTRACT

This invention provides compounds of formula I, having the structure

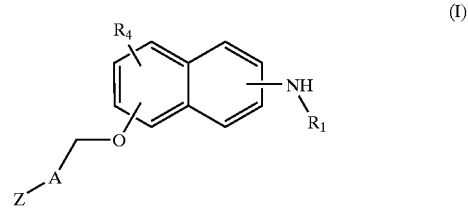

(I)

wherein $R_1$, $R_4$, A, and Z are as defined in the specification, or a pharmaceutically acceptable salt thereof, that are useful in treating metabolic disorders mediated by insulin resistance or hyperglycemia.

21 Claims, No Drawings

SUBSTITUTED NAPHTHYLENES FOR THE TREATMENT OF NON-INSULIN DEPENDENT DIABETES MELLITUS

This application claims the benefit under 35 U.S.C §119(e) to U.S. provisional application Ser. No. 60/371,373 filed Apr. 10, 2002, which is hereby incorporated by reference in its entirety.

BACKGROUND OF THE INVENTION

This invention relates to novel compounds of general formula I or pharmaceutically acceptable salts thereof, which lower plasma glucose levels and/or insulin levels in vivo and/or inhibit the production of PEPCK enzyme and/or lower glucose and/or insulin levels in cultured cells and are therefore useful in the treatment of non-insulin dependent diabetes mellitus (NIDDM).

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type 1), formerly referred to as juvenile onset diabetes since it was evident early in life, and non-insulin dependent diabetes mellitus (NIDDM or Type 2), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders. Insulin regulates glucose homeostasis mainly by acting on two targets tissues: liver and muscle. Liver is the only site of glucose production and skeletal muscle the main site of insulin mediated glucose uptake.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, a-glycosidase inhibition, antagonism of $a_2$-receptors and inhibition of gluconeogenesis. Two classes of compounds have predominated: the biguanides as represented by phenformin and the sulfonylureas as represented by tolbutamide (Orinase®). A third class of compounds which has shown antihyperglycemic activity are the thiazolidinediones. Recently a member (troglidazone) of this family was introduced for the treatment of Type 2 diabetes.

PEPCK is present at relatively high specific activity in liver, renal cortex, and white fat (R. M. O'Brien, *Diabetes Care*, 1990, 13, 327–339). It catalyzes the conversion of oxaloacetate to phosphonoenolpyruvate, the rate-limiting step in hepatic and renal gluconeogenesis, and it is essential for the synthesis of a-glycerophosphate in adipose tissue. Given that PEPCK catalyzes the rate-limiting step in gluconeogenesis, it is reasonable to conclude that the activity of the PEPCK gene determines the rate of this important metabolic process (E. Sharfir, *Frontiers In Diabetes Research*, 1998, John Libbey & Company, Ltd, pp 304–315). PEPCK activity is altered in vivo by glucagon, glucocorticoids, insulin, epinephrine, thyroxine and glucose. The primary effectors are glucagon and glucocorticoids, which increase the synthesis of PEPCK, and insulin, which decreases its synthesis. All of these effects appear to result from alterations in the amount of PEPCK mRNA, which in turn result from changes in the rate of transcription of the PEPCK gene. Gluconeogenesis rates are increased two- to three-fold in patients with NIDDM, and gluconeogenesis is the predominant mechanism responsible for fasting hyperglycemia in NIDDM (A. Consoli, et.al. *Diabetes*, 1989, 38, 550–557). Modulation of the transcription of the PEPCK gene may lead to glucose lowering in NIDDM patients.

Clinical Correlation: Compounds that inhibit or modulate glucose production in cultured hepatocytes from gluconeogenic precursors should inhibit gluconeogenesis in man and cause a reduction in the circulating plasma glucose level. Known gluconeogenic inhibitors that cause decreases in blood glucose in vivo have been shown to be active in this assay. (References: Berry M N, Edwards A M, Barritt G J. Isolated hepatocytes, preparation properties and applications in laboratory techniques in Biochemistry and Molecular Biology. 1983;65:55–63; Exton, J. H. The perfused rat liver in Methods in Enzymology XXXIX, part D (Hormone Action), pp 25–36 (1975). Eds.; J. G. Hardman and B. W. O'Malley. Goodman M N. Effect of 3-mercaptopicolinic acid on gluconeogenesis and gluconeogenic metabolite concentrations in the isolated perfused rat liver. Biochem. J. 1975;150:137–139; Jomain-Baum M, Schramm V L, Hanson R W. Mechanism of 3-mercaptopicolinic acid inhibition of hepatic phosphoenol pyruvate carboxykinase (GTP). J. Biol. Chem. 1976;251:37–44; Lowry O H, Rosebrough N J, Farr A L, Randall R J: Protein measurement with the Folin phenol reagent. J. Biol. Chem. 1951;193:265–275; Musmann T. Rapid calorimetric assay for cellular growth and survival: application to proliferation and cytotoxicity assays. J. Immunol. Meth. 1983;65: 55–63).

DESCRIPTION OF THE INVENTION

The compounds of the present invention, represented by Formula I below, act to inhibit the production of PEPCK enzyme and/or PEPCK mRNA, and/or lower glucose and/or insulin levels in cultured cells, and/or demonstrate oral antihyperglycemic activity in an animal model of NIDDM, namely the ob/ob mouse, and are useful in the treatment of non-insulin dependent diabetes mellitus (NIDDM).

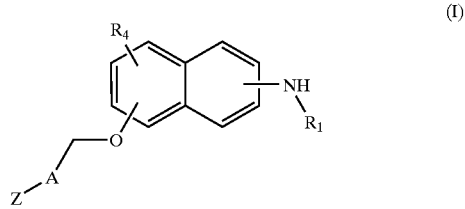

(I)

wherein:
Z is

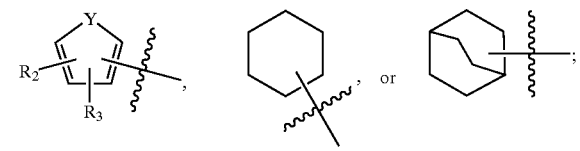

Y is selected from O, S, N, C=C, or C=N;
$R_1$ is selected from —$SO_2CF_3$, —$SO_2Ar$, —$SO_2CH_3$, —$SO_2CH_2CF_3$, —$CONH_2$, —$CSNHCH_3$, —$CONHAr$, —$COAr$, —$COCCl_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —NO$_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

R$_2$ and R$_3$ are independently selected from hydrogen, halogen, hydroxy, -alkoxy of 1–6 carbon atoms, —CF$_3$, —CN, alkyl of 1–6 carbon atoms, or —CH=CHPh; or R$_2$ and R$_3$ may be taken together as —C(CH$_3$)$_2$CH$_2$CH$_2$—C(CH$_3$)$_2$—, or —OCH$_2$CH$_2$O—; or R$_2$ and R$_3$ may be taken together as —CH=CH—CH=CH—, when A is not a bond;

R$_4$ is hydrogen or halogen,

A is a bond; or

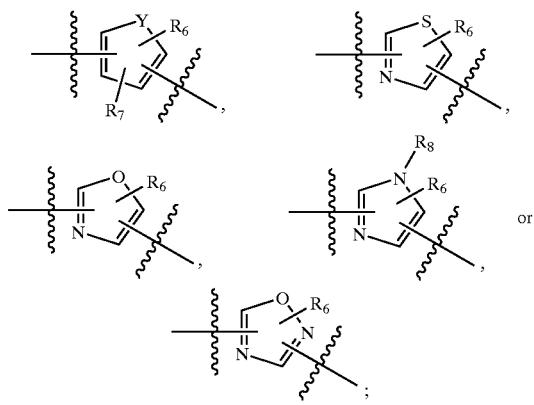

wherein R$_6$, and R$_7$ are each, independently, hydrogen, hydroxy, alkoxy of 1–6 carbon atoms, CF$_3$, CN, or alkyl of 1–6 carbon atoms;

R$_8$ is hydrogen or alkyl of 1–6 carbon atoms;

or a pharmaceutically acceptable salt form thereof.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The term alkyl includes both branched and straight chain moieties. Examples include methyl, ethyl, propyl, butyl, isopropyl, sec-butyl, tert-butyl and the like. The term halogen includes bromine, chlorine, fluorine, and iodine. The term alkylthio means —S-alkyl.

As used in accordance with this invention, the term "providing," with respect to providing a compound or substance covered by this invention, means either directly administering such a compound or substance, or administering a prodrug, derivative, or analog which will form the effective amount of the compound or substance within the body.

A first group of preferred compounds of the present invention are those of formula II:

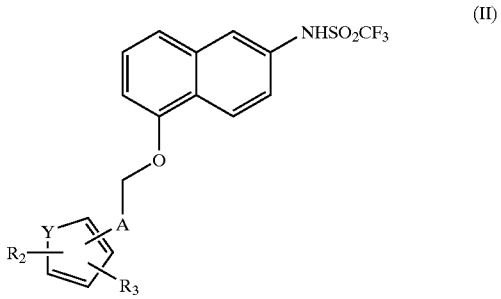

wherein,

A is

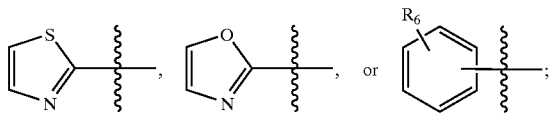

Y is —C=C—;

or a pharmaceutically acceptable salt form thereof.

A second group of preferred compounds of this invention are those of formula (III):

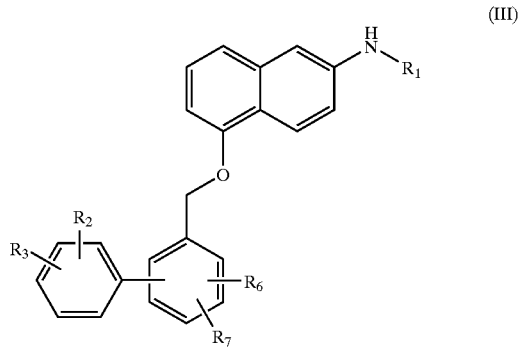

or a pharmaceutically acceptable salt form thereof.

A third group of preferred compounds of this invention comprises those of formulae (IV and (V):

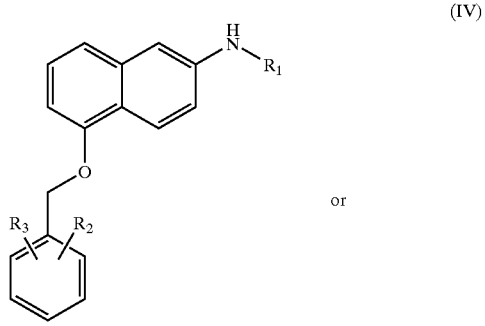

(V)

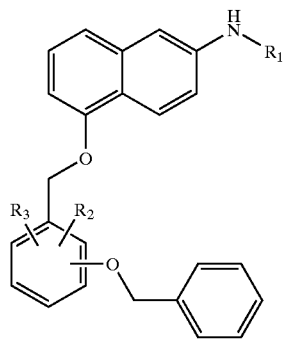

wherein:

R₁ is selected from $SO_2CF_3$, $SO_2Ar$, $SO_2CH_3$, $SO_2CH_2CF_3$, $CONH_2$, $CSNHCH_3$, $CONHAr$, $COAr$, or $COCCl_3$;

Ar represent an optionally mono- or di-substituted phenyl, naphthyl, pyridyl, or quinolyl group; and $R_2$ and $R_3$ are independently selected from the group of H, Cl, Br, F, $OCH_3$, $CF_3$, CN, or $CH_3$; or a pharmaceutically acceptable salt form thereof.

A fourth preferred group of compounds of this invention are those of formulae (VI) and (VII):

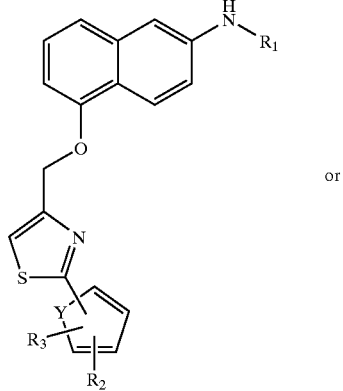

(VI)

or

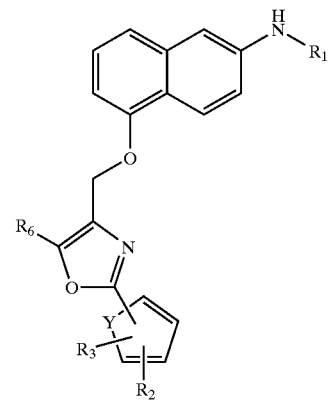

(VII)

wherein:

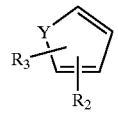

represents a group selected from:

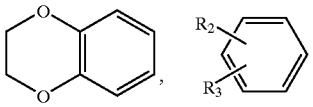 or 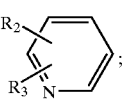;

or a pharmaceutically acceptable salt form thereof.

A fifth group of preferred compounds of this invention includes those of formula VIII:

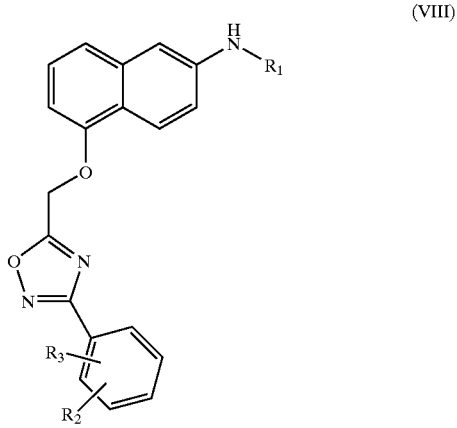

(VIII)

or a pharmaceutically acceptable salt form thereof.

Particularly preferred compounds of this invention are:

a) C,C,C-Trifluoro-N-[5-biphenyl-3-ylmethoxy)-naphthalen-2-yl]-methanesulfonamide;
b) N-[5-(3',4'-Dichloro-3-fluoro-biphenyl-4-ylmethoxy)-naphthalen-2-yl]-C,C,C-trifluoro-methanesulfonamide;
c) N-[5-(4-naphthalen-2-yl-benzyloxy-3-ylmethoxy)-naphthalen-2-yl]-C,C,C-trifluoro-methanesulfonamide;
d) C,C,C-Trifluoro-N-[5-(3-fluoro-4'-trifluoromethyl-biphenyl-4-ylmethoxy)-naphthalen-2-yl]-methanesulfonamide;
e) N-[5-(4'-tert-Butyl-3-fluoro-biphenyl-4-ylmethoxy)-naphthalen-2-yl]-C,C,C-trifluoro-methanesulfonamide;
f) N-[5-(3,4'-Dichloro-biphenyl-4-ylmethoxy)-naphthalen-2-yl]-C,C,C-trifluoro-methanesulfonamide;
g) C,C,C-Trifluoro-N-[5-(3,3',4'-trichloro-biphenyl-4-ylmethoxy)-naphthalen-2-yl]-methanesulfonamide;
h) N-{5-[2-(2,4-Difluoro-phenyl)-thiazol-4-ylmethoxy]-naphthalen-2-yl}-C,C,C-trifluoro-methanesulfonamide;
i) C,C,C-Trifluoro-N-{5-[2-(5-trifluoromethyl-pyridin-2-yl)-thiazol-4-yl-methoxy]naphthalen-2-yl}-methanesulfonamide;
j) C,C,C-Trifluoro-N-{5-[2-(4-methoxy-phenyl)-thiazol-4-ylmethoxy]-naphthalen-2-yl}-methanesulfonamide;

k) N-{5-[2-(4-trufluoromethyl-phenyl)-thiazol-4-ylmethoxy]-naphthalen-2-yl}-C,C,C-trifluoromethanesulfonamide;

l) C,C,C-Trifluoro-N-[5-(3-fluoro-biphenyl-4-ylmethoxy)-naphthalen-2-yl]-methanesulfonamide; or m) N-{5-[5-methyl-2-(4-trifluoromethylphenyl)-oxazol-4-ylmethoxy]naphthalen-2-yl}C,C,C-trifluoromethanesulfonamide The reagents used in the preparation of the compounds of this invention can be either commercially obtained or can be prepared by standard procedures described in the literature. The compounds of the present invention can be generally prepared according to the following synthetic scheme.

Scheme I

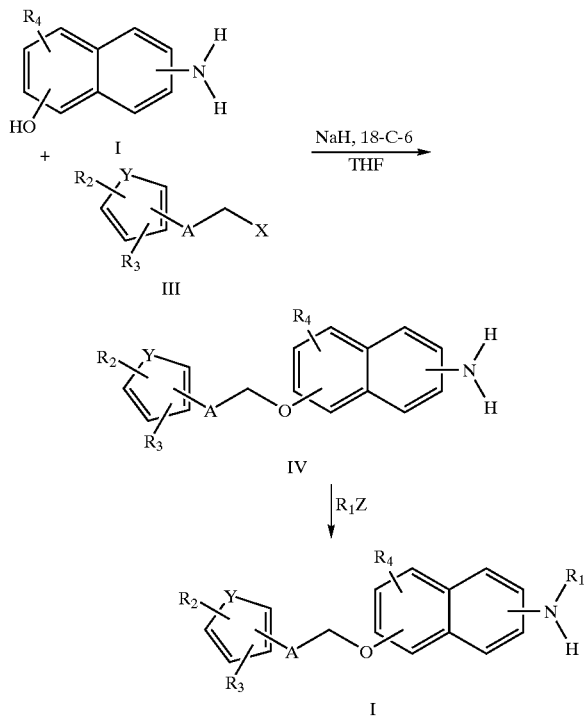

wherein:
X = Cl, Br
Z = Cl, CF3SO3

The synthesis of the title products is depicted in Scheme I. Amino alcohols of type (II) are reacted with a halo compound of type (III) (prepared as described or obtained from commercial sources) in the presence of a strong base and crown ether to provide the coupled product of type (IV). This intermediate is then reacted with the appropriate electrophile to provide the title compounds (I). These processes are well known in the art.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes. Additionally, because an association exists between insulin resistance and hypertension and between insulin resistance, hypertension and coronary artery disease, the compounds of this invention are also useful for the treatment of primary (essential) hypertension and atherosclerosis.

The ability of compounds of this invention to treat or inhibit disorders related to insulin resistance or hyperglycemia was established with representative compounds of this invention in the following pharmacological test procedures.

Inhibition of Glucose Output from Hepatocytes Isolated and Cultured from Obese Zucker (fa/fa) Rats and Their Lean Controls Culturing of Hepatocytes: Isolated hepatocytes were plated on 12 well rat-tail collagen coated plates at a cell density of 5×10(5) cells/ml (approximately 1 ml of cell suspension per well). Following a one hour attachment period in which plates were incubated in a $CO_2$ incubator at 37 deg C. (95% $O_2$, 5% $CO_2$), the supernatant containing unattached hepatocytes was removed and replaced with fresh media (1 ml/well) containing 1 $\mu$M dexamethasone and 100 pM insulin. Cells were maintained at 37 deg C. for 48 hours in a 95% $O_2$, 5% $CO_2$ environment. At the end of the first 24 hours, the media was aspirated off of the wells and replaced with fresh media containing the same concentrations of dexamethasone and insulin as described earlier.

Treatment with Drugs and Assessment of Glucose Output: Drugs were routinely added with fresh media 24 hours after the initial attachment period. Eighteen hours later, media was aspirated and 500 $\mu$l of fresh Hank's buffer, Buffer D (glucose-free) supplemented with hormones, gluconeogenic substrates and drug(s) was added to each well and incubated for 4 hours. At the end of the 4 hour incubation, media from each well was removed and assayed for glucose content using the hexokinase/glucose-6-phosphate dehydrogenase coupled assay on the Boehringer Mannheim model 911 auto analyzer. Glucose concentration was expressed as $\mu$g/ml. Three of the plates from each treated group were frozen for subsequent determination of protein content. Two plates from each treatment group were used to assess the cytotoxicity of drug(s) and other agents as determined by the MTT (tetrazolium) dye reduction method (see below).

Assessment of Cytotoxicity using MTT Dye Reduction Assay: Two plates with no insulin treatment and two plates with $10^{-8}$ M insulin treatment were used for the MTT dye reduction assay. Following removal of media from the plates for measurement of glucose output, wells were washed once with 1 ml of Hank's buffer (0.5% BSA). Aliquots of 500 ml of Hank's buffer (1.1% BSA) and 50 ml MTT solution (5 mg MTT/ml in phosphate buffered saline (PBS) filtered through 0.45 micron syringe filter) were added to each well. Plates were incubated for one hour at 37 deg C. After one hour incubation, the MTT dye solution was aspirated off and 300 ml of HCL/isopropanol solution (8 ml of 1N HCL and 192 ml of isopropanol) was added to each well. HCL/isopropanol solution was mixed by drawing liquid into a pipetman 2 to 3 times and then carefully transferred into a 96 well flat bottom plate. The 96 well plate was read on a plate reader (UV max kinetic microplate reader, Molecular Devices) at 570 nm test wavelength and 650 nm reference wavelength. The results were expressed as % inhibition from the control (lactate and glucagon treated) well.

Protein test procedure: Three plates with no insulin treatment and three plates with $10^{-8}$ M insulin treatment were used for protein determination. After supernatant has been removed for determination of glucose output the plates were frozen and stored at −20 deg C. until ready to assay for protein content. Prior to determination of protein the plates were defrosted at room temperature for 15 minutes. An aliquot of 1 ml 0.1 N NaOH was added to each well. Plates were incubated at 4 deg C. overnight. Solutions for measurement of protein content were mixed by pipetting the NaOH solution up and down several time with a 1 ml pipette and then transferring to a small polyethylene tube. Protein determination was based on that of the Pierce BCA protein assay protocol (Pierce cat. no. 23223). A set of protein standards (0.2, 0.4, 0.6, 0.8, and 1 mg/ml BSA) was prepared by serial dilution of 1 mg/ml bovine serum albumin with 0.1 N NaOH, and 40 μl of each standard, or control blank was pipetted into a 96-well plate in duplicate. Each unknown protein sample (40 μl) was tested in triplicate. An aliquot of 200 μl of BCA protein assay reagent (consisting of 50 parts Reagent A with 1 part Reagent B) was added to each well. Samples were mixed with a Titertek pipette. The microtiter plate was covered with sealing tape and incubated at room temperature for 1 hour. After incubation, the sealing tape was removed and absorbance measured on a plate reader (Uvmax kinetic microplate reader, Molecular Devices) at 570 nm. A standard curve was prepared by plotting the blank-corrected absorbance against known protein concentrations, and protein concentrations were then determined for each unknown.

Buffers:

Buffer A 50 ml 10XHBSS
400 ml ddH2O
2.38 g Hepes
95 mg EGTA
900 mg glucose
2.36 ml 7.5% NaHCO$_3$
pH to 7.4 with 1 N NaOH
q.s. to 500 ml with ddH$_2$O qs to 2L Buffer B 50 ml 10XHBSS
430 ml ddH$_2$O
2.45 mg Hepes
366.3 mg CaCl$_2$.2H$_2$O
891 mg glucose
2.34 ml 7.5% NaHCO$_3$
qs to 500 ml
100 mg collagenase Buffer C (10 × solv.)
1800 ml ddH2O
95.2 g Hepes
142.6 g NaCl
7.5 g KCL
4.8 g MgSO$_4$
11.4 g K$_2$HPO$_4$.3H$_2$O Buffer D 50 ml 10 × Buffer C
400 ml ddH$_2$O
59 mg CaCl$_2$.2H$_2$O
1.01 g NaHCO$_3$
BSA (0.2–1.1%) if necessary
pH to 7.4
qs to 500 ml Measurements and Calculations: Glucose output was calculated as μg glucose/mg protein/hour, and inhibition of glucose output was calculated as percent inhibition of glucose output when compared to glucagon stimulated cells. Cytotoxicity was determined using the MTT dye reduction assay and data were expressed as percent inhibition of MTT dye reduction compared to control cells. For some compounds of interest multiple point dose response curves were assessed and half-maximal inhibitory concentrations (IC$_{50}$) were calculated for both inhibition of glucose output and MTT dye reduction. Insulin potentiation was assessed by calculating the difference in percent inhibition of glucose output with and without drug(s) in the presence of the same insulin concentration.

Statisical Analysis: Two factors ANOVA with interaction was used to compare different compounds to control and other compounds within each concentration of insulin. The same procedure was used to compare effects of insulin alone. The ICx (where x equals 25,50 etc.) was determined for insulin, drug and insulin+drug using multi point logistic four parameter dose response curves. In addition another parameter (insulin interaction with drug) was estimated using the same technique. Confidence intervals (Wald) were determined using student's t distribution.

Reference Compound: Mercaptopicolinc acid (inhibitor of PEPCK activity)

References:

Berry M N, Edwards A M, Barritt G J. Isolated hepatocytes, preparation properties and applications in laboratory techniques in Biochemistry and Molecular Biology. 1983;65:55–63.

Exton, J H. The perfused rat liver in Methods in Enzymology XXXIX, part D (Hormone Action), pp 25–36 (1975). Eds. J. G. Hardman and B. W. O'Malley.

Goodman M N. Effect of 3-mercaptopicolinic acid on gluconeogenesis and gluconeogenic metabolite concentrations in the isolated perfused rat liver. Biochem. J. 1975;150:137–139, Jomain-Baum M, Schramm V L, Hanson R W. Mechanism of 3-mercaptopicolinic acid inhibition of hepatic phosphoenol pyvrate carboxykinase (GTP). J. Biol. Chem.

Musmann T. Rapid colorimetric assay for cellular growth and survival: application to proliferation and cytotoxicity assays. J. Immunol. Meth. 1983;65:55–63.

Smith P K, Krohn R I, Hermanson G T, Mallia A K, Gartner F H, Provenjano M D, Fujimoto E K, Goeke N M, Olson B J, and Klenk D C. Measurement of Protein Using Bincinchoninic Acid. Analo. Biochem. 1985;150:76–85.

The following table summarizes the results obtained using representative compounds of this invention.

| EXAMPLE | IC$_{50}$ |
|---|---|
| 5 | 6.3 μM |
| 14 | 10.4 μM |
| 27 | 7.0 μM |
| 30 | 3.1 μM |
| 31 | 2.6 μM |
| 46 | 2.8 μM |
| 52 | 12 μM |
| 53 | 9.5 μM |
| 57 | 1.5 μM |

Hypoglycemic Effect in Diabetic OB/OB Mice

Procedure: In each study, male or female ob/ob (C57 B1/6J) mice and their mean litermates (ob/+ or +/+, Jackson Laboratories) ages 2 to 5 months (10 to 65 g) were randomized according to plasma glucose into 4 groups of 10 mice. The mice were housed 5 per cage and were maintained on normal rodent chow with water ad libitum. Mice receive compound daily by gavage (suspended in 0.5 ml of 0.5% methyl cellulose); dissolved in the drinking water; or admixed in the diet. The dose of compounds given ranges from 2.5 to 200 mg/kg body weight/day. Body weight of fed animals was measured at the beginning of each week and doses for the entire week were calculated using this weight and were expressed in terms of the active moiety of the compound. Control mice receive vehicle only.

On the morning of Day 4, 7 or 14 two drops of blood (approximately 50 ul) were collected into sodium fluoride containing tubes either from the tail vein or after decapitation. For those studies in which the compound was administered daily by gavage the blood samples were collected four hours after compound administration.

Measurements: The plasma was isolated by centrifugation and the concentration of glucose was measured enzymatically on an Abbott V. P. Analyzer and the plasma concentration of insulin was determined by radioimmunoassay (Heding, 1972)

Calculations: For each mouse, the percentage change in plasma glucose on Day 4, 7 or 14 was calculated relative to the mean plasma glucose of the vehicle treated mice. Analysis of variance followed by Dunnett's Comparison Test (one-tailed) was used to estimate the significant difference between the plasma glucose values from the control group and the individual compound treated groups (CMS SAS Release 5.18). A compound will be considered active if the difference has a $p<0.05$.

Clinical Correlation: The non-insulin dependent diabetic (NIDDM) syndrome can be typically characterized by obesity, hyperglycemia, abnormal insulin secretion, hyperinsulinemia and insulin resistance. The genetically obese-hyperglycemic ob/ob mouse exhibits many of these metabolic abnormalities and is a useful model for hypoglycemic agents to treat NIDDM (Coleman, 1978).

Reference Compound: Ciglitazone (5-(4-(1-methylcyclohexylmethoxy)-benzyl)-2,4-dione, Upjohn) and sodium metavanadate (NaVO3) at doses of 100 and 20 mg/kg/day, respectively, produce a significant lowering in plasma glucose (Brichard et al. 1990; Chang et al. 1983.

References:

Brichard, S., Bailey, C. and Henquin, J.: Marked improvement of glucose homeostasis in diabetic ob/ob mice given oral vanadate Diabetes 39: 1326–1332,1990.

Chang, A., Wyse, B., Gilchrist, B., Peterson, T. and Diani, A.: Ciglitazone, a new hypoglycemic agent. I. Studies in ob/ob and db/db mice, diabetic Chinese hamsters, and normal and streptozotocin-diabetic rats. Diabetes 32: 830–838,1983.

Coleman, D.: Obese and diabetes: Two mutant genes causing diabetes-obesity syndromes in mice. Diabetologia 14: 141–148,1978.

Heding, L. G.: Determination of total serum insulin (IRI) in insulin-treated diabetic patients. Diabetologia 8:260–266, 1972.

The following table summarizes the results obtained using representative compounds of this invention.

| REDUCTION IN PLASMA GLUCOSE | | |
| --- | --- | --- |
| EXAMPLE | Day 1 (6 hr) p.o. | Day 3 (6 hr) p.o. |
| 27 | | −31% (10 mg/kg) |
| 30 | −6% (25 mg/kg) | −11% (25 mg/kg) |
| 57 | | −33% (10 mg/kg) |
| 4 | −28% (10 mg/kg) | −37% (10 mg/kg) |
| 31 | −23% (5 mg/kg) | −22% (5 mg/kg) |
| 25 | −22% (10 mg/kg) | −24% (10 mg/kg) |
| 81 | −28% (5 mg/kg) | −33% (5 mg/kg) |

Based on the results obtained in the standard pharmacological test procedures, the compounds of this invention are useful in treating metabolic disorders related to insulin resistance or hyperglycemia, typically associated with obesity or glucose intolerance. More particularly, the compounds of this invention are useful in the treatment or inhibition of type II diabetes, and in modulating glucose levels in disorders such as type I diabetes. The compounds of this invention are also useful in the treatment of primary (essential) hypertension and atherosclerosis. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Compounds of this invention may be administered neat or with a pharmaceutical carrier to a patient in need thereof. The pharmaceutical carrier may be solid or liquid.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

N-[5-(4-Bromo-benzyloxy)-naphthalen-2-yl]-C,C,C-trifluoromethanesulfonamide

Step 1. Preparation of 5-(Bromo-phenyl-4-ylmethoxy)-naphthalen-2-yl-amine

General Procedure for Ether Coupling

To a solution of 0.30 g (12.5 mmol) of 95% sodium hydride in 50 ml of THF was added dropwise a 50 mL solution of 1.59 g (10 mmol) of 6-amino-1-naphthol at 0° C. 1 drop of 15-crown-5 and/or DMSO was then added, and after stirring for 0.5 hr 2.7 g (13 mmol) of 4-bromobenzyl chloride was added in one portion. The mixture was stirred at room temperature for 5 hr. At the end of this time, the solution was concentrated and the residue washed with 15 ml of saturated ammonium chloride and extracted 2 times with 30 mL of ethyl acetate. The organic layers were combined, dried (MgSO$_4$) and concentrated. The crude solid was chromatographed on silica gel eluting with 40% ethyl acetate:hexane. Concentration yielded 1.91 g (62%) of the product as a brown solid, used in the next step without further purification.

NMR (200 Mhz, CDCl$_3$) δ 8.17 (d, J=8 Hz, 1H ArH), 7.56 (d, J=8 Hz, 2H, ArH), 7.38 (d, J=8 Hz, 2H, ArH), 7.25 (m, 2H, ArH), 6.91 (m, 2H, ArH), 6.61 (d, J=8 Hz, 1H, H6), 5.15 (s, 2H, OCH2), 3.84 (bs, 2H, NH).

Step 2. Preparation of the Title Compound

General Procedure for Triflation of Amines

To a 250 mL flask charged with 150 mL of methylene chloride is added 1.03 mL (7.41 mmol) of triethyl amine and 1.89 g (6.18 mmol) of the product from Step 1. The flask was cooled to −20° C. where upon a solution of 1.14 mL (6.80 mmol) of trifluoromathane sulfonic anhydride in 25 mL of methylene chloride was added dropwise under nitrogen atmosphere. After ½ hr, 2 mL of a 1M solution tetra n-butyl ammonium flouride was added and the mixture stirred for 16 hr. At the end of this time, the solution was concentrated, diluted with 50 mL of saturated ammonium chloride and extracted 2 times with ethyl acetate. The organic layers were combined, dried (MgSO$_4$) and concentrated. The crude solid was chromatographed on silica gel eluting with 30% ethyl acetate:hexane. Concentration yielded 1.83 g (68%) of the title compound as a brown oil, used in the next step without further purification.

NMR (400 MHz, DMSO-d6) δ 11.80 (bs, 1H, NH), 7.45 (d, J=8 Hz, 2H ArH), 7.18 (d, J=8 Hz, 2H, ArH), 7.7 (t, J=8 Hz, 1H, H5), 7.17 (d, J=8 Hz, 1H, H4), 7.15 (s, 1H, H2), 7.11 (d, J=8 Hz, 1H, H6), 4.51 (s, 2H, OCH2), 3.65 (t, J=7 Hz, 2H, OCH2), 2.85 (t, J=7 Hz, 2H, ArCH2).

EXAMPLE 2

N-[5-(3',4'-Dichloro-biphenyl-4-ylmethoxy)-naphthalen-2-yl]-C,C,C-trifluoro-methanesulfonamide General Procedure for Aryl Coupling To a 50 mL flask charged with 20 mL toluene and 5 mL EtOH was added 250 mg (0.57 mmol) of the product from Example 1, 153 mg (0.80 mmol) of 3,4-dichloro benzene boronic acid, and 3 mL of aqueous 5% potassium carbonate solution. The flask was stirred and degassed for 5 minutes with a steady stream of nitrogen, after which 35 mg (0.03 mmol) of tetrakis(triphenylphosphine) palladium(0) was added. The mixture was heated to 70° C. for 18 hr under an atmosphere of nitrogen. At the end of this time the solution was concentrated and diluted with 30 mL of saturated ammoniun chloride solution. The mixture was extracted 2× with ethyl acetate and the organic layers combined and dried (MgSO$_4$), then concentrated. The crude solid was chromatographed on silica gel eluting with 30% ethyl acetate:hexane. Concentration yielded 0.192 mg (68%) of the title compound as an oil, which was triturated with hexane to form a solid. The solid was recrystallized from ethyl acetate:hexane to yield 0.17 g of the title product as colorless crystals, m.p. 98–100° C.

NMR (400 MHz, DMSO-d6) δ 11.80 (bs, 1H, NH), 8.24 (d, J=8 Hz, 1H, H8), 7.93 (s, 1H, H1), 7.62–7.98 (m, 7H, ArH), 7.36–7.51 (m, 3H, ArH), 7.18 (d, J=8 Hz, 1H, H3), 5.38 (s, 2H, OCH2).

Anal. Calcd. for C24H16C12F3N1O3S1: C, 54.76; H, 3.06; N, 2.66. Found: C, 54.28; H, 3.22; N, 2.57.

C,C,C-Trifluoro-N-[5-(4'-methoxy-biphenyl-4-ylmethoxy)-naphthalen-2-yl]-methanesulfonamide, 165–167° C., NMR (400 MHz, DMSO-d6) δ11.80 (bs, 1H, NH), 8.22 (d, J=8 Hz, 1H, H8), 7.77 (s, 1H, H1), 7.53–7.69 (m, 6H, ArH), 7.38–7.55 (m, 3H, ArH), 7.18 (d, J=8 Hz, 1H, H3), 7.04 (d, J=8 Hz, 2H, ArH), 5.36 (s, 2H, OCH2), 3.81 (s, 3H, OCH3).

Anal. Calcd. for C25H20F3N1O4S1: C, 61.60; H, 4.13; N, 2.87. Found: C, 61.41; H, 4.33; N, 2.73.

EXAMPLE 3

C,C,C-Trifluoro-N-[5-(2-fluoro,4-bromophen-2-yl-methoxy)-naphthalen-2-yl]-methanesulfonamide Step 1. Preparation of 5-(2-fluoro,4-bromophen-2-yl-methoxy)-naphthalen-2-yl-amine To a solution of 0.30 g (12.5 mmol) of 95% sodium hydride and 1 drop of 15-crown-5 in 150 mL of THF was added dropwise a solution of 1.59 g (10 mmol) of 6-amino-1-naphthol at 0° C. After stirring for 0.5 hr 2.8 g (13 mmol) of 4-bromo,2-fluoro benzyl bromide was added in one portion. The mixture was stirred at room temperature for 5 hr. At the end of this time, the solution was concentrated and the residue washed with 10 ml of saturated ammonium chloride and extracted 2 times with 40 mL of ethyl acetate. The organic layers were combined, dried (MgSO$_4$) and concentrated. The crude solid was chromatographed on silica gel eluting with 40% ethyl acetate:hexane. Concentration yielded 2.2 g (65%) of the product as a brown solid, used in the next step without further purification.

Step 2. Preparation of the Title Compound

To a 250 mL flask charged with 150 mL of methylene chloride is added 1.1 mL (7.92 mmol) of triethyl amine and 2.2 g (6.60 mmol) of the product from Step 1. The flask was cooled to −20° C. where upon a solution of 1.2 mL (7.92 mmol) of trifluoromathane sulfonic anhydride in 25 mL of methylene chloride was added dropwise under nitrogen atmosphere. After ½ hr, 2 mL of a 1M solution tetra n-butyl ammonium flouride was added and the mixture stirred for 16 hr. At the end of this time, the solution was concentrated, diluted with 50 mL of saturated ammonium chloride and extracted 2 times with ethyl acetate. The organic layers were combined, dried (MgSO$_4$) and concentrated. The crude solid was chromatographed on silica gel eluting with 30% ethyl acetate:hexane. Concentration yielded 1.8 g (68%) of the title compound as a brown solid. The product can be recrystallized from ethyl acetate:hexane to yield 0.87 of light brown solid, m.p. 126–128° C.

NMR (200 MHz, CDCl3) δ 11.80 (bs, 1H, NH), 8.32 (d, J=8 Hz, 1H, H8), 7.72 (s, 1H, H1), 7.23–7.53 (m, 6H, ArH), 6.73 (d, J=8 Hz, 1H, H3), 5.23 (s, 2H, OCH2).

EXAMPLE 4

C,C,C-Trifluoro-N-[5-(3-fluoro-biphenyl-4-ylmethoxy)-naphthalen-2-yl]-methanesulfonamide To a 50 mL flask charged with 20 mL toluene and 5 mL EtOH was added 250 mg (0.54 mmol) of the product from Example 1, 91 mg (0.75 mmol) of phenylboronic acid, and 3 mL of aqueous 5% potassium carbonate solution. The flask was stirred and degassed for 5 minutes with a steady stream of nitrogen, after which 35 mg (0.03 mmol) of tetrakis (triphenylphosphine) palladium(0) was added. The mixture was heated to 70° C. for 18 hr under an atmosphere of nitrogen. At the end of this time the solution was concentrated and diluted with 30 mL of saturated ammoniun chloride solution. The mixture was extracted 2× with ethyl acetate and the organic layers combined and dried ($MgSO_4$), then concentrated. The crude solid was chromatographed on silica gel eluting with 30% ethyl acetate:hexane. Concentration yielded 0.165 mg (68%) of the title compound as a solid. The solid was recrystallized from ethyl acetate:hexane to yield 0.13 g of the title product as colorless crystals, m.p. 123–125° C.

NMR (400 MHz, DMSO-d6) δ12.15 (bs, 1H, NH), 8.20 (d, J=8 Hz, 1H, H8), 7.36–7.54 (m, 12H, ArH), 7.18 (d, J=8 Hz, 1H, ArH), 5.38 (s, 2H, OCH2).

Anal. Calcd. for C24H17F4N1O3S1: C, 60.63; H, 3.60; N, 2.94. Found: C, 60.25; H, 3.54; N, 2.88.

EXAMPLE 5

C,C,C-Trifluoro-N-[5-(3-fluoro-4'-trifluoromethyl-biphenyl-4-ylmethoxy)-naphthalen-2-yl]-methanesulfonamide Following the procedure of Example 4, the product of Example 3 and trifloromethyl benzene boronic acid was converted to the title product, m.p. 98–100° C.

NMR (400 MHz, DMSO-d6) δ12.15 (bs, 1H, NH), 8.18 (d, J=8 Hz, 1H, H8), 7.96(d, J=8 Hz, 2H, ArH), 7.82 (d, J=8 Hz, 2H, ArH), 7.58–7.74 (m, 5H, ArH), 7.46(m, 3H, ArH), 7.38 (d, J=8 Hz, 1H, ArH), 7.14(d, J=8 Hz, 1H, H6) 5.41 (s, 2H, OCH2).

Anal. Calcd. for C25H16F7N1O3S1: C, 55.25; H, 2.97; N, 2.58. Found: C, 55.12; H, 3.18; N, 2.47.

EXAMPLE 6

N-[5-(4'-tert-Butyl-3-fluoro-biphenyl-4-ylmethoxy)-naphthalen-2-yl]-C,C,C-trifluoro-methanesulfonamide Following the procedure of Example 4, the product of Example 3 and 4-t-butyl benzene boronic acid was converted to the title product, m.p. 162–164° C.

NMR (400 MHz, DMSO-d6) δ12.18 (bs, 1H, NH), 8.21 (d, J=8 Hz, 1H, H8), 7.45–7.78 (m, 8H, ArH), 7.20 (d, J=8 Hz, 1H, ArH), 7.17 (d, J=8 Hz, 1H, H6), 5.41 (s, 2H, OCH2), 1.36 (s, 9H, C(CH3)).

Anal. Calcd. for C28H25F4N1O3S1: C, 63.27; H, 4.74; N, 2.64. Found: C, 62.78; H, 4.75; N, 2.53.

EXAMPLE 7

N-[5-(3,4'-Difluoro-biphenyl-4-ylmethoxy)-naphthalen-2-yl]-C,C,C-trifluoro-methanesulfonamide Following the procedure of Example 4, the product of Example 3 and 4-fluoro benzene boronic acid was converted to the title product, m.p. 134–136° C.

NMR (400 MHz, DMSO-d6) δ12.08 (bs, 1H, NH), 8.19 (d, J=8 Hz, 1H, H8), 7.28–7.82 (m, 11H, ArH), 7.17 (d, J=8 Hz, 1H, H6), 5.41 (s, 2H, OCH2).

Anal. Calcd. for C24H16F5N1O3S1: C, 58.42; H, 3.27; N, 2.84. Found: C, 58.08; H, 3.28; N, 2.68.

EXAMPLE 8

N-[5-(4'-Chloro-3-fluoro-biphenyl-4-ylmethoxy)-naphthalen-2-yl]-C,C,C-trifluoro-methanesulfonamide Following the procedure of Example 4, the product of Example 3 and 4-chloro benzene boronic acid was converted to the title product, m.p. 151–153° C.

NMR (400 MHz, DMSO-d6) δ12.08 (bs, 1H, NH), 8.22 (d, J=8 Hz, 1H, H8), 7.26–7.78 (m, 10H, ArH), 7.38 (d, J=8 Hz, 1H, ArH), 7.18 (d, J=8 Hz, 1H, H6), 5.41 (s, 2H, OCH2).

Anal. Calcd. for C24H16Cl1F4N1O3S1: C, 56.53; H, 3.16; N, 2.75. Found: C, 56.85; H, 3.15; N, 2.54.

EXAMPLE 9

N-[5-(3',4'-Dichloro-3-fluoro-biphenyl-4-ylmethoxy)-naphthalen-2-yl]-C,C,C-trifluoro-methanesulfonamide Following the procedure of Example 4, the product of Example 3 and 3,4-dichloro benzene boronic acid was converted to the title product, m.p. 172–174° C.

NMR (400 MHz, DMSO-d6) δ12.08 (bs, 1H, NH), 8.17 (d, J=8 Hz, 1H, H8), 8.04 (s, 1H, ArH), 7.43–7.78 (m, 8H, ArH), 7.38 (d, J=8 Hz, 1H, ArH), 7.16 (d, J=8 Hz, 1H, H6), 5.41 (s, 2H, OCH2).

EXAMPLE 11

N-[5-(4-Chloro-4'-fluoro-biphenyl-3-ylmethoxy)-naphthalen-2-yl]-C,C,C-trifluoro-methanesulfonamide The title compound was prepared from 2-Chloro, (4-fluorphenyl) benzyl chloride according to the procedure of Example 1, m.p. 155–157 DMSO: δ 12.1(s, 1H), 7.0–8.3 (m, 13H, arom), 5.4 (s, 2H). CHN 56.53, 3.16, 2.75. Found 56.13, 3.23, 2.48.

EXAMPLE 12

N-[5-(4'-Fluoro-4'-methoxy-biphenyl-3-ylmethoxy)-naphthalen-2-yl]-C,C,C-trifluoro-methanesulfonamide was prepared from 2-Fluoro, (4-fluorphenyl) benzyl chloride according to the procedure of Example 1, m.p. 125–127 DMSO: δ 12.1(s, 1H), 7.0–8.3(m, 13H, arom), 5.4 (s, 2H). CHN 59.40, 3.79, 2.77. Found 59.45, 4.37, 3.08.

EXAMPLE 13

N-[5-(3',5'-Dichloro-biphenyl-3-ylmethoxy)-naphthalen-2-yl]-C,C,C-trifluoro-methanesulfonamide The title compound was prepared from 3-(3,5-dichloro phenyl) benzyl chloride according to the procedure of Example 1, m.p. 142–143° C. DMSO: δ 12.1(s, 1H), 7.0–8.3 (m, 13H, arom), 5.4 (s, 2H)DMSO: δ 12.1(s, 1H), 7.0–8.3 (m, 13H, arom), 5.36 (s, 2H). CHN 54.30, 3.13, 2.64 (0.25 M $H_2O$). Found 54.08, 2.98, 2.66.

EXAMPLE 14

N-[5-(4-naphthalen-2-yl-benzyloxy-3-ylmethoxy)-naphthalen-2-yl]-C,C,C-trifluoro-methanesulfonamide The title compound was prepared from 4-(2-Naphthyl) benzyl chloride according to the procedure of Example 1, m.p. 142–143° C. DMSO: δ 12.1(s, 1H), 7.0–8.3(m, 13H, arom), 5.4 (s, 2H) DMSO: δ 12.1(s, 1H), 7.0–8.3(m, 17H, arom), 5.38 (s, 2H). CHN 66.26, 3.97, 2.76. Found 66.96, 4.39, 2.92.

EXAMPLE 15

N-[5-(3-fluoro-4'-methoxy biphenyl-4-ylmethoxy)-naphthalen-2-yl]-C,C,C-trifluoro-methanesulfonamide The title compound was prepared from the product of Example 3 and 4-methoxy phenyl boronic acid according to the procedure of Example 2, m.p. 108–11° C. DMSO: δ 12.1(s, 1H), 7.0–8.3(m, 13H, arom), 5.4 (s, 2H)DMSO: δ 11.9(s, 1H), 7.0–8.2(m, 13H, arom), 5.36 (s, 2H), 3.8(s, 3H). CHN 57.36, 4.04, 2.68 (1 M $H_2O$). Found 57.76, 3.55, 2.46.

EXAMPLE 16

N-[5-(3',5'-Dichloro-biphenyl-4-ylmethoxy)-naphthalen-2-yl]-C,C,C-trifluoro-methanesulfonamide The title compound was prepared from the product of Example 1 and 3,5-dichloro phenyl boronic acid according to the procedure of Example 2, m.p. 138–140 DMSO: δ 12.1(s, 1H), 7.0–8.3(m, 13H, arom), 5.38 (s, 2H). CHN 53.84, 3.20, 2.62 (0.5 M $H_2O$) Found 53.97, 3.02, 2.40.

EXAMPLE 17

N-[5-(4'-Fluoro-biphenyl-3-ylmethoxy)-naphthalen-2-yl]-C,C,C-trifluoro-methanesulfonamide The title compound was prepared from 3-(4-fluoro phenyl) benzyl chloride according to the procedure of Example 1, m.p. 110–112° C. DMSO: δ 12.1(s, 1H), 7.0–8.3 (m, 14H, arom), 5.36 (s, 2H). CHN 60.63, 3.60, 2.94. Found 61.03, 3.74, 2.73.

EXAMPLE 18

N-[5-(4'-Fluoro-biphenyl-4-ylmethoxy)-naphthalen-2-yl]-C,C,C-trifluoro-methanesulfonamide The title compound was prepared from the product of Example 1 and 4-florophenyl boronic acid according to the procedure of Example 2, m.p. 139–140° C. DMSO: δ 12.0 broad (s, 1H), 7.0–8.3(m, 14H, arom), 5.36 (s, 2H). CHN 60.63, 3.60, 2.94. Found 60.60, 3.50, 2.83.

EXAMPLE 19

N-[5-(Biphenyl-2-ylmethoxy)-naphthalen-2-yl]-C,C,C-trifluoromethanesulfonamide was prepared from 2-phenyl benzyl chloride The title compound was prepared according to the procedure of Example 1, m.p. 119–121° C. NMR (400 MHz, DMSO) δ: 8.08 (d, J=9.0 Hz, 1H); 7.28 (m, 14H); 5.15 (s, 2H). Anal. Calcd. for $C_{24}H_{18}F_3NO_3S$: C, 63.01; H, 3.97; N, 3.06. Found: C, 63.36; H, 4.25; N, 3.25.

EXAMPLE 20

C,C,C-Trifluoro-N-[5-(4'-methoxy-biphenyl-3-ylmethoxy)-naphthalen-2-yl]-methanesulfonamide The title compound was prepared from 3-(4-methoxyphenyl) benzyl chloride according to the procedure of Example 1, m.p. 123–125.

$^1$H NMR (400 MHz, DMSO) δ: 8.24 (d, 1H, J=9.0 Hz); 7.39 (m, 13H); 5.36 (s, 2H).

Anal. Calcd. for $C_{25}H_{20}F_3NO_4S$: C, 61.6; H, 4.14; N, 2.87. Found: C, 57.48; H, 4.14; N, 2.76; 487.5016 EI m/z 487.

EXAMPLE 21

N-[5-(4'-Chloro-4-methoxy-biphenyl-3-ylmethoxy)-naphthalen-2-yl]-C,C,C-trifluoromethanesulfonamide The title compound was prepared from 2-Methoxy-(5-chlorophenyl) benzyl chloride according to the procedure of Example 1, m.p. 155–157° C.

$^1$H NMR (400 MHz, DMSO) δ: 8.17 (d, J=9.0 Hz, 1H); 7.46 (m, 12H); 5.66 (s, 2H); 3.88 (s, 3H).

Anal. Calcd. for $C_{25}H_{19}ClF_3NO_4S$: C, 57.53; H, 3.67; N, 2.68. Found: C, 57.16; H, 3.85; N, 2.51; 521.947 (+)FAB m/z 522 (M+H), 544 (M+Na).

EXAMPLE 22

N-[5-(4'-Chloro-biphenyl-4-ylmethoxy)-naphthalen-2-yl]-C,C,C-trifluoromethanesulfonamide The title compound was prepared from the product of Example 1 and 4-chlorophenyl boronic acid according to the procedure of Example 2, m.p. 131–133.

$^1$H NMR (DMSO) δ: 8.24 (d, J=9.0 Hz, 1H); 7.61 (m, 12H); 7.10 (d, J=7.5 Hz, 1H); 5.37 (s, 2H).

Anal. Calcd. for $C_{24}H_{17}ClF_3NO_3S$: C, 58.6; H, 3.48; N, 2.85. Found: C, 56.27; H, 3.46; N, 2.84; 491.9198 EI m/z 491.

EXAMPLE 23

C,C,C-Trifluoro-N-[5-(2-methyl-biphenyl-3-ylmethoxy)-naphthalen-2-yl]-methanesulfonamide The title compound was prepared from 2-Methyl, 3-phenyl benzyl chloride according to the procedure of Example 1, m.p. 124–125° C.

$^1$H NMR (DMSO) δ: 8.22 (d, J=9.0 Hz, 1H); 7.74 (d, J=2.2 Hz, 1H); 7.37 (m, 12H); 5.34 (s, 2H); 2.25 (s, 3H).

Anal. Calcd. for $C_{25}H_{20}F_3NO_3S$: C, 63.69; H, 4.28; N, 2.97. Found: C, 62.91; H, 4.92; N, 2.81.

EXAMPLE 24

C,C,C-Trifluoro-N-[5-(4-pyridin-2-yl-benzyloxy)-naphthalen-2-yl]-methanesulfonamide The title compound was prepared from 4-(2-pyridyl) benzyl chloride according to the procedure of Example 1, m.p.119–120.

$^1$H NMR (400 MHz, DMSO) δ: 8.01 (m, 11H); 7.08 (d, J=6.8 Hz, 1H); 5.38 (s, 2H).

Anal. Calcd. for $C_{23}H_{17}F_3N_2O_3S$: C, 60.26; H, 3.74; N, 6.11. Found: C, 58.66; H, 3.84; N, 5.81; 458.4628 EI m/z 458.

EXAMPLE 25

N-[5-(3'-Chloro-biphenyl-4-ylmethoxy)-naphthalen-2-yl]-C,C,C-trifluoromethanesulfonamide The title compound was prepared from the product of Example 1 and 3-chlorophenyl boronic acid according to the procedure of Example 2, m.p. 170–171° C.

¹H NMR (400 MHz, DMSO) δ: 8.26 (d, J=9.0 Hz, 1H); 7.58 (m, 12H); 7.09 (d, 1H, J=6.6 Hz); 5.34 (s, 2H).

Anal. Calcd. for $C_{24}H_{17}ClF_3N_2O_3S$: C, 58.60; H, 3.48; N, 5.69. Found: C, 57.95; H, 3.30; N, 2.63; 491.9152 (−)ESI m/z 490 (M−H).

EXAMPLE 26

C,C,C-Trifluoro-N-[5-(6-fluoro-4'-methoxy-biphenyl-3-ylmethoxy)-naphthalen-2-yl]-methanesulfonamide The title compound was prepared from 4-Fluoro, 5-(4-methoxy phenyl) benzyl chloride according to the procedure of Example 1, m.p. 132–133° C.

¹H NMR (400 MHz, DMSO) δ: 8.22 (d, J=9.0 Hz, 1H); 7.39 (m, 12H); 5.34 (s, 2H); 3.81 (s, 3H).

Anal. Calcd. for $C_{25}H_{19}F_4NO_4S$: C, 59.03; H, 3.78; N, 2.75. Found: C, 58.50; H, 3.88; N, 3.02; 505.4865 (+)ESI m/z 523 (M+NH4).

EXAMPLE 27

C,C,C-Trifluoro-N-[5-biphenyl-3-ylmethoxy)-naphthalen-2-yl]-methanesulfonamide

The title compound was prepared from 4-phenyl benzyl chloride according to the procedure of Example 1, m.p. 122–125° C.

Anal. Calcd. for $C_{24}H_{18}F_3NO_3S$: C, 63.01; H, 3.97; N, 3.06. Found: C, 63.19; H, 4.01; N, 2.92.

NMR (400 MHz, DMSO) δ: 8.25 (d, J=9 Hz, 1H, ArH), 7.62–7.74 (m, 7H, ArH), 7.34–7.51 (M, 6H, ArH), 7.02 (d, J=7 Hz, 1H, H2), 5.36 (s, 2H, OCH2).

EXAMPLE 28

C,C,C-Trifluoro-N-[5-(2-chloro,4-bromophen-2-yl-methoxy)-naphthalen-2-yl]-methanesulfonamide Step 1. Preparation of 5-(2-chloro,4-bromophen-2-yl-methoxy)-naphthalen-2-yl-amine To a solution of 0.30 g (12.5 mmol) of 95% sodium hydride and 1 drop of 15-crown-5 in 150 mL of THF was added dropwise a solution of 1.59 g (10 mmol) of 6-amino-1-naphthol at 0° C. After stirring for 0.5 hr 3.1 g (13 mmol) of 4-bromo,2-chloro benzyl chloride was added in one portion. The mixture was stirred at room temperature for 5 hr. At the end of this time, the solution was concentrated and the residue washed with 10 ml of saturated ammonium chloride and extracted 2 times with 40 mL of ethyl acetate. The organic layers were combined, dried (MgSO4) and concentrated. The crude solid was chromatographed on silica gel eluting with 40% ethyl acetate:hexane. Concentration yielded 2.3 g (64%) of the product as a brown solid, used in the next step without further purification Step 2 Preparation of the Title Compound To a 100 mL flask charged with 50 mL of methylene chloride is added 0.30 mL (2.0 mmol) of triethyl amine and 0.63 g (1.72 mmol) of the product from Step 1. The flask was cooled to −20° C. where upon a solution of 0.32 mL (1.82 mmol) of trifluoromathane sulfonic anhydride in 10 mL of methylene chloride was added dropwise under nitrogen atmosphere. After ½ hr, 1 mL of a 1M solution tetra n-butyl ammonium flouride was added and the mixture stirred for 16 hr. At the end of this time, the solution was concentrated, diluted with 20 mL of saturated ammonium chloride and extracted 2 times with ethyl acetate. The organic layers were combined, dried (MgSO4) and concentrated. The crude solid was chromatographed on silica gel eluting with 30% ethyl acetate:hexane. Concentration yielded 1.8 g (68%) of the title compound as a brown solid.

NMR (200 MHz, CDCl3) δ 11.80 (bs, 1H, NH), 8.32 (d, J=8 Hz, 1H, H8), 7.63 (s, 1H, H1), 7.23–7.53 (m, 6H, ArH), 6.73 (d, J=8 Hz, 1H, H3), 5.23 (s, 2H, OCH2).

EXAMPLE 29

N-[5-(3-Chloro-biphenyl-4-ylmethoxy)-naphthalen-2-yl]-C,C,C-trifluoro-methanesulfonamide To a 50 mL flask charged with 20 mL toluene and 5 mL EtOH was added 250 mg (0.51 mmol) of the product from Example 28, 91 mg (0.75 mmol) of phenylboronic acid, and 3 mL of aqueous 5% potassium carbonate solution. The flask was stirred and degassed for 5 minutes with a steady stream of nitrogen, after which 35 mg (0.03 mmol) of tetrakis (triphenylphosphine) palladium(0) was added. The mixture was heated to 70° C. for 18 hr under an atmosphere of nitrogen. At the end of this time the solution was concentrated and diluted with 30 mL of saturated ammoniun chloride solution. The mixture was extracted 2× with ethyl acetate and the organic layers combined and dried (MgSO4), then concentrated. The crude solid was chromatographed on silica gel eluting with 30% ethyl acetate:hexane. Concentration yielded 0.165 mg (68%) of the title compound as a solid. The solid was recrystallized from ethyl acetate:hexane to yield 0.12 g of the title product as colorless crystals, m.p. 131–134° C.

NMR (400 MHz, DMSO-d6) δ12.15 (bs, 1H, NH), 8.22 (d, J=8 Hz, 1H, H8), 7.37–7.84 (m, 12H, ArH), 7.16 (d, J=8 Hz, 1H, ArH), 5.42 (s, 2H, OCH2).

Anal. Calcd. for C24H17Cl1F3N1O3S1: C, 57.60; H, 3.480; N, 2.85. Found: C, 57.72; H, 3.41; N, 2.69.

EXAMPLE 30

C,C,C-Trifluoro-N-[5-(3,3',4'-trichloro-biphenyl-4-ylmethoxy)-naphthalen-2-yl]-methanesulfonamide The title compound was prepared from the product of Example 28 and 3,4-dichlorophenyl boronic acid according to the procedure of Example 29, m.p. 169–170° C.

NMR (400 MHz, DMSO-d6) δ12.15 (bs, 1H, NH), 8.23 (d, J=8 Hz, 1H, H8), 8.04 (d, J=2 Hz, 1H, ArH), 7.93 (d, J=2 Hz, 1H, ArH), 7.71–7.82 (m, 4H, ArH), 7.43–7.56 (m, 3H, ArH), 7.40 (d, J=8 Hz, 1H, ArH), 7.17 (d, J=8 Hz, 1H, H6), 5.42 (s, 2H, OCH2).

Anal. Calcd. for $C_{24}H_{15}Cl3F3N1O3S1$: C, 51.40; H, 2.70; N, 2.50. Found: C, 51.26; H, 2.83; N, 2.51.

EXAMPLE 31

N-[5-(3,4'-Dichloro-biphenyl-4-ylmethoxy)-naphthalen-2-yl]-C,C,C-trifluoro-methanesulfonamide The title compound was prepared from the product of Example 28 and 4-chlorophenyl boronic acid according to the procedure of Example 29 m.p. 176–178° C.

NMR (400 MHz, DMSO-d6) δ12.15 (bs, 1H, NH), 8.23 (d, J=8 Hz, 1H, H8), 7.88 (s, 1H, ArH), 7.71–7.84 (m, 5H, ArH), 7.43–7.58 (m, 4H, ArH), 7.40 (d, J=8 Hz, 1H, ArH), 7.16 (d, J=8 Hz, 1H, H6), 5.42 (s, 2H, OCH2).

Anal. Calcd. for C24H16Cl2F3N1O3S1: C, 54.76; H, 3.06; N, 2.66. Found: C, 54.65; H, 2.96; N, 2.60.

EXAMPLE 32

N-[5-(4-Cyclohexyl-benzyloxy)-naphthalen-2-yl}-C,
C,C-trifluoro-methanesulfonamide The title compound was prepared from 4-cyclohexyl benzyl chloride according to the procedure of Example 1, m.p. 108–110° C. DMSO: δ 12.1 (s, 1H), 7.0–8.2(m, 10H, arom), 5.25 (s, 2H), 1.1–1.8(m, 11H). NMR 62.19, 5.22, 3.02. Found 62.19, 5.30, 2.96.

EXAMPLE 33

N-[5-(4-Tert-butyl-benzyloxy)-naphthalen-2-yl}-C,
C,C-trifluoro-methanesulfonamide The title compound was prepared from 4-t-butyl benzyl chloride according to the procedure of Example 1, oil, NMR: DMSO: δ 12.1 (s, 1H), 7.0–8.2(m, 10H, arom), 5.25 (s, 2H), 1.3(s, 9H). CHN 60.40, 5.07, 3.20. Found 60,46, 5.24, 2.84.

EXAMPLE 34

N-[5-(2,4-Dichloro-benzyloxy)-naphthalen-2-yl}-C,
C,C-trifluoro-methanesulfonamide The title compound was prepared from 2,4-dichloro benzyl chloride according to the procedure of Example 1, m.p. 142–144° C. DMSO: δ 12.1 (s, 1H), 7.0–8.2(m, 9H, arom), 5.32 (s, 2H). CHN 48.02, 2.69, 3.11. Found 47.46, 2.77, 2.90.

EXAMPLE 35

N-[5-(3-Chloro-4-methoxy-benzyloxy)-naphthalen-2-yl}-C,C,C-trifluoro-methanesulfonamide The title compound was prepared from 3-chloro benzyl chloride according to the procedure of Example 1, m.p. 129–130° C. DMSO: δ 12.1 (s, 1H), 7.0–8.2(m, 9H, arom), 5.25 (s, 2H), 3.85 (s, 3H). CHN 51.55, 3.58, 2.88. Found 51.19, 3.39, 3.14.

EXAMPLE 36

N-[5-(4-Bromo-2-fluoro-benzyloxy)-naphthalen-2-yl}-C,C,C-trifluoromethanesulfonamide The title compound was prepared from 4-Bromo,2-fluoro benzyl bromide according to the procedure of Example 1, m.p. 123–125° C. DMSO: δ 12.1 (s, 1H), 7.0–8.2(m, 9H, arom), 5.3 (s, 2H). CHN 45.20, 2.53, 2.93. Found 45.05, 2.54, 2.74.

EXAMPLE 37

N-[5-(4-Benzyloxy-benzyloxy)-naphthalen-2-yl}-C,
C,C-trifluoromethanesulfonamide The title compound was prepared from 4-benzyloxy benzyl chloride according to the procedure of Example 1, oil, DMSO: δ 12.1 (s, 1H), 6.9–8.2(m, 15H, arom), 5.25 (s, 2H), 5.15 (s, 2H), CHN 61.60, 4.14, 2.87. Found 61.21, 4.09, 2.82.

EXAMPLE 38

N-[5-(3-Bromo-benzyloxy)-naphthalen-2-yl}-C,C,C-trifluoromethanesulfonamide

The title compound was prepared from 3-Bromo benzyl bromide according to the procedure of Example 1, m.p. 113–115° C. DMSO: δ 12.1 (s, 1H), 7.0–8.3(m, 10H, arom), 5.3 (s, 2H) NMR 46.97, 2.85, 3.04. Found 47.12, 3.01, 3.00.

EXAMPLE 39

N-[5-(2,6-Dichloro-pyridin-4-yl)-naphthalen-2-yl]-
C,C,C-trifluoromethanesulfonamide The title compound was prepared from 2,6-Dichloro benzyl chloride according to the procedure of Example 1 m.p. 185–187° C. CDCl$_3$: δ 7.0 (s, 1H), 6.7–8.4(m, 8H, arom), 5.25 (s, 2H). CHN 45.25, 2.46, 6.21. Found 44.87, 2.66, 5.99.

EXAMPLE 40

N-[5-(4-Trifluoromethoxy-benzyloxy)-naphthalen-2-yl}-C,C,C-trifluoromethanesulfonamide The title compound was prepared from 4-Trifluoromethyl benzyl chloride according to the procedure of Example 1, m.p. 80–82° C. DMSO: δ 12.1 (s, 1H), 7.0–8.3(m, 10H, arom), 5.35 (s, 2H). CHN 49.04, 2.82, 3.01. Found 49.55, 2.93, 2.92.

EXAMPLE 41

N-[5-(4-Iodo-benzyloxy)-naphthalen-2-yl}-C,C,C-
trifluoromethanesulfonamide

The title compound was prepared from 4-Bromo,2-fluoro benzyl bromide according to the procedure of Example 1 was prepared from 4-Iodo benzyl bromide according to the procedure of Example 1, m.p. 120–122° C. DMSO: δ 12.1 (s, 1H), 7.0–8.3(m, 10H, arom), 5.28 (s, 2H). CHN 42.62, 2.58, 2.76. Found 44.83, 3.23, 2.39.

EXAMPLE 42

C,C,C-Trifluoro-N-{5-[6-(4-fluoro-phenyl)-pyridin-
2-ylmethoxy]-naphthalen-2-yl}-methanesulfonamide Step 1. Preparation of 2-methyl, 6-trifluoromethanesulfonyl pyridine To a flask charged with 2.18 g (20 mmol) of 6-hydroxy, 2-methyl pyridine and 3.06 ml (22 mmol) of triethyl amine dissolved in 200 mL of methylene chloride was added dropwise a solution of of 3.70 ml (22 mmol) of trifluoromethane sulfonic anhydride in 50 mL of methylene chloride at 0° C. After 2 h, the solution was concentrated, and the residue washed with water and extracted twice with 100 mL of ethyl acetate. After upon drying and concentrating, the dark oil was subjected to flash chromatography on silica gel. Elution with 20% ethyl acetate:hexane yielded a light yellow oil used immediately in subsequent steps without further purification.

Step 2. Preparation of 2-methyl, 6-(4-fluorophenyl) pyridine.

2.8 g (10.8 mmol) of the product obtained from step 1, 1.4 g (8.92 mmol) of 4-fluorobenzene boronic acid and 2.84 g (13.4 mmol) of potassium phosphate were placed in a flask along with 80 mL of dioxane. The solution was degassed with nitrogen, whereupon 85 mg of tetrakis (triphenylphosphine) palladium was added. The solution was heated to 70° C. for 24 hr. At the end of this time, the solution was concentrated, and the residue washed with water and extracted with ethyl acetate (2×50 mL). The combined extracts were dried and concentrated then the residue chromatographed over silica gel. Elution with 20% ethyl acetate:hexane yielded 1.8 g (89%) of a light yellow oil.

NMR (200 MHz, CDCl3) δ 7.96 (m, 2H, ArH), 7.64 (t, J=8 Hz, 1H, ArH), 7.45 (d, J=8 Hz, 1H, ArH), 7.16 (m, 3H, ArH), 2.63 (s, 3H, CH3).

Step 3. Preparation of 2-chloromethyl, 6-(4-fluorophenyl) pyridine 0.60 g (3.2 mmol) of the product of step 2 was dissolved in 50 mL of carbon tetrachloride, along with 0.54 g (3.5 mmol) of N-chloro succinimide and a catalytic amount of benzoyl peroxide. After refluxing for 20 hr, the solution was concentrated and filtered through a plug of silica gel eluting with 20% ethyl acetate:hexane. The resulting oil was contaminated with ~10% of unreacted starting material and was used in the next step without further purification.

NMR (200 MHz, CDCl3) δ 7.96 (m, 2H, ArH), 7.63 (m, 1H, ArH), 7.43 (m, 1H, ArH), 7.17 (m, 3H, ArH), 4.72 (s, 2H, CH2Cl).

Step 4. Preparation of the Title Compound

The product from step 3 was converted to the title compound following the procedure of Example 1 (yield 42%), m.p. 173–174° C.

NMR (400 MHz, DMSO-d6) δ12.05 (bs, 1H, NH), 8.35 (d, J=8 Hz, 1H, ArH), 8.18 (m, 2H, ArH), 7.94 (m, 2H, ArH), 7.73(s, 1H, ArH), 7.62 (d, J=8 Hz, 1H, ArH), 7.30–7.55 (m, 5H, ArH), 7.18 (s, 1H, ArH), 5.44 (s, 2H, OCH2).

Anal. Calcd. for C23H16F4N2O3S1: C, 57.98; H, 3.38; N,5.88. Found: C, 58.23; H, 3.37; N, 5.82.

EXAMPLE 43

C,C,C-Trifluoro-N-{5-[6-(4-trifluoromethyl-phenyl)-pyridin-2-ylmethoxy]-naphthalen-2-yl}-methanesulfonamide The title compound was prepared according to the procedure of example 42, except that trifluoromethyl benzeneboronic acid was used in step 2 in place of 4-fluoro benzeneboronic acid, m.p. 180–182° C.

NMR (400 MHz, DMSO-d6) δ12.05 (bs, 1H, NH), 8.35 (m, 3H, ArH), 8.08 (m, 2H, ArH), 7.84 (d, J=8 Hz, 2H, ArH), 7.75(s, 1H, ArH), 7.62 (d, J=8 Hz, 1H, ArH), 7.41–7.55 (m, 3H, ArH), 7.18 (s, 1H, ArH), 5.44 (s, 2H, OCH2).

Anal. Calcd. for C24H16F6N2O3S1: C, 54.76; H, 3.06; N,5.32. Found: C, 54.80; H, 3.30; N, 5.15.

EXAMPLE 44

N-{5-[2-(4-Chloro-phenyl)-thiazol-4-ylmethoxy]-naphthalen-2-yl}-C,C,C-trifluoro-methanesulfonamide The title compound was prepared from 4-chloromethyl-2-(4-chloro) phenyl thiazole following the procedure of Example 1 m.p. 151–153° C.

NMR (400 MHz, DMSO-d6) δ 12.10 (bs, 1H, NH), 8.25 (d, J=8 Hz, 1H ArH), 7.96 (m, 3H, ArH), 7.75 (s, 1H, N=CH—S), 7.42–7.57 (m, 4H, ArH), 7.38 (d, J=8 Hz, 1H, ArH), 7.18 (d, 1H, H6), 5.42 (s, 2H, OCH2).

Anal. Calcd. for C21H14Cl1F3N2O3S2: C, 50.56; H, 2.83; N, 5.62. Found: C, 50.41; H, 3.44; N, 5.31.

EXAMPLE 45

C,C,C-Trifluoro-N-{5-[2-(4-fluoro-phenyl)-thiazol-4-ylmethoxy]-naphthalen-2-yl}-methanesulfonamide The title compound was prepared from 4-chloromethyl-2-(4-fluoro phenyl) thiazole following the procedure of Example 1 m.p. 170–173° C.

NMR (400 MHz, DMSO-d6) δ 12.10 (bs, 1H, NH), 8.25 (d, J=8 Hz, 1H ArH), 8.12 (m, 2H, ArH), 7.92(s, 1H, ArH), 7.75 (s, 1H, N=CH—S), 7.31–7.57 (m, 5H, ArH), 7.18 (d, 1H, H6), 5.42 (s, 2H, OCH2).

Anal. Calcd. for C21H14F4N2O3S2: C, 52.28; H, 2.92; N, 5.81. Found: C, 52.36; H, 2.77; N, 5.51.

EXAMPLE 46

N-{5-[2-(2,4-Difluoro-phenyl)-thiazol-4-ylmethoxy]-naphthalen-2-yl}-C,C,C-trifluoro-methanesulfonamide The title compound was prepared from 4-chloromethyl-2-(2,4-difluoro phenyl) thiazole following the procedure of Example 1, m.p. 191–192° C.

NMR (400 MHz, DMSO-d6) δ 12.10 (bs, 1H, NH), 8.24 (m, 2H, ArH), 8.14 (s, 1H, ArH), 7.92(s, 1H, ArH), 7.75 (s, 1H, N=CH—S), 7.41–7.57 (m, 3H, ArH), 7.38 (d, J=8 Hz, 1H, ArH), 7.31 (t, J=8 Hz, 1H, ArH), 7.18 (d, 1H, H6), 5.42 (s, 2H, OCH2).

Anal. Calcd. for C21H13F5N2O3S2: C, 50.4; H, 2.62; N, 5.60. Found: C, 50.16; H, 2.69; N, 5.35.

EXAMPLE 47

N-{5-[2-(4-tert-Butyl-phenyl)-thiazol-4-ylmethoxy]-naphthalen-2-yl}-C,C,C-trifluoro-methanesulfonamide The title compound was prepared from 4-chloromethyl-2-(4-t-butyl phenyl) thiazole following the procedure of Example 1, m.p. 174–175° C.

NMR (400 MHz, DMSO-d6) δ 12.10 (bs, 1H, NH), 8.25 (d, J=8 Hz, 1H, ArH), 7.85 (m, 3H, ArH), 7.77 (s, 1H, N=CH—S), 7.45–7.57 (m, 4H, ArH), 7.38 (d, J=8 Hz, 1H, ArH), 7.18 (d, J=8 Hz, 1H, H6), 5.42 (s, 2H, OCH2), 1.24 (s, 9H, C(CH3)3).

Anal. Calcd. for C25H23F3N2O3S2: C, 57.68; H, 4.45; N, 5.38. Found: C, 58.16; H, 4.71; N, 5.01.

EXAMPLE 48

N-{5-[2-(3-Chloro-4-fluoro-phenyl)-thiazol-4-ylmethoxy]-naphthalen-2-yl}-C,C,C-trifluoro-methanesulfonamide The title compound was prepared from 4-chloromethyl-2-(3-chloro,4-fluoro phenyl) thiazole following the procedure of Example 1 m.p. 169–170° C.

NMR (400 MHz, DMSO-d6) δ 12.10 (bs, 1H, NH), 8.23 (d, J=8 Hz, 1H, ArH), 8.17(d, J=8 Hz, 1H, ArH), 7.98 (m, 2H, ArH), 7.77 (s, 1H, N=CH—S), 7.45–7.57 (m, 3H, ArH), 7.38 (d, J=8 Hz, 1H, ArH), 7.18 (d, J=8 Hz, 1H, H6), 5.42 (s, 2H, OCH2).

Anal. Calcd. for C21H13F4N2O3S2: C, 48.80; H, 2.54; N, 5.42. Found: C, 48.95; H, 2.82; N, 5.12.

EXAMPLE 49

N-{5-[2-(6-Chloro-pyridin-3-yl)-thiazol-4-ylmethoxy]-naphthalen-2-yl}-C,C,C-trifluoro-methanesulfonamide The title compound was prepared from 4-chloromethyl-2-(6-chloro-pyridin-3-yl) thiazole following the procedure of Example 1, m.p. 154–156° C.

NMR (400 MHz, DMSO-d6) δ 12.10 (bs, 1H, NH), 9.01(s, 1H, ArH), 8.39 (d, J=8 Hz, 1H, ArH), 8.26 (d, J=8 Hz, 1H, ArH), 8.17(d, J=8 Hz, 1H, ArH), 7.78 (s, 1H,

N=CH—S), 7.45–7.57 (m, 2H, ArH), 7.40 (d, J=8 Hz, 1H, ArH), 7.18 (d, J=8 Hz, 1H, H6), 5.42 (s, 2H, OCH2).

Anal. Calcd. for C21H13F4N2O3S2: C, 48.05; H, 2.62; N, 8.41. Found: C, 47.86; H, 3.09; N, 8.28.

EXAMPLE 50

N-{5-[2-(2,3-Dihydro-benzo[1,4]dioxin-2-yl)-thiazol-4-ylmethoxy]-naphthalen-2-yl}-C,C,C-trifluoro-methanesulfonamide The title compound was prepared from 4-chloromethyl-2-(2,3-dihydro-benzo[1,4]dioxin-2-yl) thiazole following the procedure of Example 1, m.p. 183–185° C.

NMR (400 MHz, DMSO-d6) δ 12.10 (bs, 1H, NH), 8.23 (d, J=8 Hz, 1H, ArH), 7.93 (s, 1H, ArH), 7.76 (s, 1H, ArH), 7.43–7.58 (m, 3H, ArH), 7.18 (d, J=8 Hz, 1H, N=CH—S), 7.03 (m, 1H, ArH), 6.91 (m, 3H, ArH), 5.79 (m, 1H, OCH), 5.39 (s, 2H, OCH2), 4.38–4.59 (m, 2H, OCH2).

Anal. Calcd. for C23H17F3N2O5S2: C, 52.87; H, 3.28; N, 5.36. Found: C, 52.55; H, 2.98; N, 5.25.

EXAMPLE 51

C,C,C-Trifluoro-N-[5-(2-phenyl-thiazol-4-ylmethoxy)-naphthalen-2-yl]-methanesulfonamide The title compound was prepared from 4-chloromethyl-2-phenyl thiazole following the procedure of Example 1, m.p. 89–99° C.

$^1$H NMR (400 MHz, DMSO) δ: 8.26 (d, J=9.2 Hz, 1H); 7.57 (m, 11H); 5.43 (s, 2H).

Anal. Calcd. for $C_{21}H_{15}F_3N_2O_3S_2$: C, 54.84; H, 3.49; N, 5.92. Found: C, 54.69; H, 3.68; N, 5.71; 464.4883 EI m/z 464.

EXAMPLE 52

C,C,C-Trifluoro-N-{5-[2-(5-trifluoromethyl-pyridin-2-yl)-thiazol-4-yl-methoxy]naphthalen-2-yl}-methanesulfonamide The title compound was prepared from 4-chloromethyl-2-(5-trifluoromethyl-pyridin-2-yl) thiazole following the procedure of Example 1, m.p. 197–198° C.

$^1$H NMR (400 MHz, DMSO) δ: 9.06 (s, 1H); 8.30 (m, 3H); 8.15 (s 1H); 7.73 (d, J=2.2 Hz, 1H); 7.45 (m, 3H); 7.18 (d, J=7.2 Hz, 1H); 5.48 (s, 2H).

Anal. Calcd. for $C_{21}H_{13}F_8N_3O_3S_2$: C, 47.28; H, 2.46; N, 7.78. Found: C, 47.31; H, 2.68; N, 7.72; 533.474 EI m/z 533.

EXAMPLE 53

C,C,C-Trifluoro-N-{5-[2-(4-methoxy-phenyl)-thiazol-4-ylmethoxy]-naphthalen-2-yl}-methanesulfonamide The title compound was prepared from 4-chloromethyl-2-(4-methoxy-phenyl) thiazole following the procedure of Example 1 m.p. 151–152° C.

$^1$H NMR (400 MHz, DMSO) δ: 8.26 (d, J=9.0 Hz, 1H); 7.47 (m, 10H); 5.84 (s, 2H); 3.82 (s, 3H).

Anal. Calcd. for $C_{22}H_{17}F_3N_2O_4S_2$: C, 54.41; H, 4.00; N, 5.35. Found: C, 53.97; H, 4.06; N, 5.03; 494.5156 EI m/z 494.

EXAMPLE 54

N-{5-[2-(2-Chloro-phenyl)-thiazol-4-ylmethoxy]-naphthalen-2-yl}-C,C,C-trifluoromethanesulfonamide The title compound was prepared from 4-chloromethyl-2-(2-chloro-phenyl) thiazole following the procedure of Example 1, m.p. 128–129° C.

$^1$H NMR (400 MHz, DMSO) δ: 8.26 (d, J=9.0 Hz, 1H); 7.70 (m, 10H); 5.47 (s, 2H).

Anal. Calcd. for $C_{21}H_{14}ClF_3NO_3S_2$: C, 50.55; H, 2.83; N, 2.81. Found: C, 49.69; H, 2.70; N, 5.22; 498.9324 (−)ESI m/z 497 (M−H).

EXAMPLE 55

C,C,C-Trifluoro-N-{5-[2-(4-trifluoromethoxy-phenyl)-thiazol-4-yl-methoxy]-naphthalen-2-yl}-methanesulfonamide The title compound was prepared from 4-chloromethyl-2-(4-trifluoromethoxyphenyl) thiazole following the procedure of Example 1, m.p. 131–132° C.

$^1$H NMR (400 MHz, DMSO) δ: 8.26 (d, J=9.0 Hz, 1H); 8.09 (ddd, $J_1$=11.9 Hz, $J_2$=5.1 Hz, $J_3$=2.9 Hz, 2H); 7.97 (s, 1H); 7.73 (d, J=2.2 Hz, 1H); 7.45 (m, 5H); 7.17 (d, J=6.8 Hz, 1H); 5.43 (s, 2H).

Anal. Calcd. for $C_{22}H_{14}F_6N_2O_4S_2$: C, 48.18; H, 2.57; N, 5.11. Found: C, 48.24; H, 2.81; N, 4.82; 548.483 EI m/z 548.

EXAMPLE 56

N-{5-[5-Bromo-2-(4-fluoro-phenyl)-thiazol-4-ylmethoxy]-naphthalen-2-yl}-C,C,C-trifluoromethanesulfonamide The title compound was prepared from 4-chloromethyl-2-(4-fluorophenyl) thiazole following the procedure of Example 1, m.p. 139–140° C.

$^1$H NMR (400 MHz, DMSO) δ: 8.13 (d, J=9.2 Hz, 1H); 7.67 (m, 8H); 7.19 (d, J=7.2 Hz, 1H); 5.35 (s, 2H).

Anal. Calcd. for $C_{21}H_{13}BrF_4N_2O_3S_2$: C, 43.38; H, 2.34; N, 4.74. Found: C, 43.51; H, 2.22; N, 4.66; 561.3755 (−)ESI m/z 559 (M−H).

EXAMPLE 57

N-{5-[2-(4-trufluoromethyl-phenyl)-thiazol-4-ylmethoxy]-naphthalen-2-yl}-C,C,C-trifluoro-methanesulfonamide The title compound was prepared from 4-chloromethyl-2-(4-trifluoromethylphenyl) thiazole following the procedure of Example 1, m.p. 155–157° C.

$^1$H NMR (DMSO-d$_6$, 400 MHz) δ: 8.39 (d, J=8 Hz, 1H, ArH); 8.17 (d, J=8 Hz, 2H, ArH); 7.73 (m, 3H, ArH); 7.46 (m, 3H, ArH); 7.35 (d, J=8 Hz, 1H, ArH); 6.97 (m, 2H, ArH and NH); 5.43 (s, 2H, OCH2).

Anal. Calcd. for C22H14F6N2O3S2: C, 49.63; H, 2.65; N, 5.26. Found: C, 49.98; H, 3.01; N, 4.66.

EXAMPLE 58

N-{5-[5-(4-trifluoromethyl-phenyl)-[1,2,4]-oxadiazol-5-ylmethoxy)-naphthalen-2-yl}-C,C,C-trifluoro-methanesulfonamide General procedure for preparation of 3-chloromethyl-[1,2,4] oxadiazoles Step 1. To a solution of 13.8 g of hydroxylamine hydrochloride in 30 mL of water was added 10.6 g of sodium carbonate. The mixture was stirred until everything was dissolved. Then 15 mL of chloroacetonitrile was added dropwise over a 15 min period (with exterior cooling). Stirred 1 h and then worked up by extracting twice with ether. Concentrated to give 10.8 g of chloroacetamide oxime. Used without further purification on subsequent step.

Step 2. To a solution of 3.0 g (27.6 mmol) of chloroacetamide oxime in 50 mL of dry dichloromethane at 0° C. was added 4.6 mL (33.1 mmol) of triethylamine followed by the dropwise addition of 4.52 mL (30.4 mmol) of 4-trifluoromethylbenzoyl chloride. Monitored via TLC for complete reaction (~2 h). Worked up by pouring into water and extracting with ethyl acetate several times. The combined organic layers were washed with 2 N hydrochloric acid, saturated sodium bicarbonate, and brine. Dried over anhydrous sodium sulfate, decanted, and concentrated in vacuo to give a thick residue. Residue was dissolved in 100 mL of toluene and refluxed, removing water via a Dean-Stark trap. After reaction was complete, the solvent was removed in vacuo to give an orange residue. Flash chomatography of the residue on a silica column eluting with 5–20% ethyl acetate hexane, gave after concentration, 4.5 g (62%) of pure 3-chloromethyl-5-(4-trifluoromethylphenyl)-1,2,4-oxadiazole.

Following the General Procedures of Example 1, the product from step 2 above was converted to the title product NMR(DMSO-$d_6$, 400 MHz) δ 12.2 (s, 1H), 7.1–8.4(m, 10H, arom), 5.6 (s, 2H).

The following compounds were synthesized from their corresponding acid chlorides according to the above procedure of Example 56:

EXAMPLE 59

N-{5-[5-(4-tert-Butyl-phenyl)-[1,2,4]-oxa diazol-5-ylmethoxy)-naphthalen-2-yl}-C,C,C-trifluoro-methanesulfonamide The title compound was prepared from 4-t-butyl benzoyl chloride, m.p. 154–155 NMR (DMSO-$d_6$, 400 MHz) δ 12.1 (s, 1H), 7.1–8.3 (m, 10H, arom), 5.54 (s, 2H), 1.3(s, 9H). CHN 54.43, 3.48, 9.07. Found 54.13, 3.48, 8.75.

EXAMPLE 60

N-[5-(5-Adamantan-1-yl-[1,2,4]oxadiazol-3-ylmethoxy)-naphthalen-2-yl]-C,C,C-trifluoro-methanesulfonamide The title compound was prepared from adamantoyl chloride, m.p. 60–62 NMR (DMSO-$d_6$, 400 MHz) δ 8.9(s, 1H), 6.9–8.1(m, 6H, arom), 5.4 (s, 2H), 3.7(t, 2H), 1.7–2.1 (m, 15H) CHN 56.80, 4.77, 8.28 ($BU_4N$). Found 59.46, 6.00, 7.89.

EXAMPLE 61

N-{5-[5-(4-cyano-phenyl)-[1,2,4]-oxadiazol-5-ylmethoxy)-naphthalen-2-yl}-C,C,C-trifluoro-methanesulfonamide The title compound was prepared from 4-cyano benzoyl chloride, m.p. 184–185° C. NMR (DMSO-$d_6$, 400 MHz) δ 12.1 (s, 1H), 7.1–8.4(m, 10H, arom), 5.6 (s, 2H). CHN 49.41, 3.36, 10.98 (2 M $H_2O$). Found 49.72, 2.65, 10.43.

EXAMPLE 62

N-{5-[5-(3-methoxy-phenyl)-[1,2,4]-oxadiazol-5-ylmethoxy)-naphthalen-2-yl}-C,C,C-trifluoro-methanesulfonamide The title compound was prepared from 3-methoxy benzoyl chloride, m.p. 138–140° C. NMR (DMSO-$d_6$400 MHz) δ 12.1 (s, 1H), 7.1–8.3(m, 10H, arom), 5.56 (s, 2H), 3.85(s, 3H). CHN 52.61, 3.36, 8.77. Found 52.44, 3.34, 8.70.

EXAMPLE 63

N-{5-[5-(3-trifluoromethyl-phenyl)-[1,2,4]-oxadiazol-5-ylmethoxy)-naphthalen-2-yl}-C,C,C-trifluoro-methanesulfonamide The title compound was prepared from 3-trifluoromethyl benzoyl chloride, m.p. 107–108° C. NMR (DMSO-$d_6$, 400 MHz) δ 12.2 (s, 1H), 7.1–8.5(m, 10H, arom), 5.6 (s, 2H) CHN 48.75, 2.53, 8.12. Found 48.46, 2.71, 7.90.

EXAMPLE 64

N-{5-[5-(4-methoxy-phenyl)-[1,2,4]-oxadiazol-5-ylmethoxy)-naphthalen-2-yl}-C,C,C-trifluoro-methanesulfonamide The title compound was prepared from 4-t-methoxy benzoyl chloride, m.p. 146–148° C. NMR (DMSO-$d_6$, 400 MHz) δ 12.1 (s, 1H), 7.1–8.3(m, 10H, arom), 5.53 (s, 2H), 3.85 (s, 3H) CHN 52.61, 3.36, 8.77. Found 52.33, 3.60, 8.34.

EXAMPLE 65

C,C,C-Trifluoro-N-{5-[3-(4-fluoro-phenyl)-[1,2,4]oxadiazol-5-yl-methoxy]-naphthalen-2-yl}-methanesulfonamide The title compound was prepared from 4-fluoro benzoyl chloride, m.p. 131–132° C. NMR (DMSO-$d_6$, 400 MHz) δ: 8.24 (d, J=9.0 Hz, 1H); 7.74 (m, 8H); 7.13 (d, J=7.5 Hz, 1H); 5.81 (s, 2H) Anal. Calcd. for $C_{20}H_{13}F_4N_3O_4S$: C, 51.40; H, 2.80; N, 8.99. Found: C, 50.75; H, 3.09; N, 8.53.

EXAMPLE 66

C,C,C-Trifluoro-N-{5-[3-(3-trifluoromethyl-phenyl)-[1,2,4]oxadiazol-5-ylmethoxy]-naphthalen-2-yl}-methanesulfonamide The title compound was prepared from 3-trifluoro benzoyl chloride m.p. 155–156° C. NMR (DMSO-$d_6$, 400 MHz) δ: 8.32 (d, J=7.9 Hz, 1H); 7.86 (m, 8H); 7.15 (d, J=7.7 Hz, 1H); 5.84 (s, 2H).

Anal. Calcd. for $C_{20}H_{13}F_4N_3O_4S$: C, 48.75; H, 2.53; N, 8.12. Found: C, 48.56; H, 2.54; N, 7.99; (+)FAB m/z 518 (M+H).

EXAMPLE 67

N-5-(3-thiophen-2-yl)-[1,2,4]oxadiazol-5-ylmethoxy)-naphthalen-2-yl}-C,C,C-trifluoro-methanesulfonamide The title compound was prepared from 2-thiopheneacetyl chloride m.p. 157–159° C. DMSO: δ 12.0 (s, 1H), 7.0–8.3 (m, 9H, arom), 5.77 (s, 2H), 3.75 (t, 2H), 2.91(t, 2H). CHN 47.47, 2.65, 9.23. Found 47.34, 2.57, 9.03.

EXAMPLE 68

N-{5-[3-(4-bromo-2-fluoro-phenyl)-[1,2,4]-oxadiazol-5-ylmethoxy)-naphthalen-2-yl}-C,C,C-trifluoro-methanesulfonamide The title compound was prepared from 4-bromo-2-fluoro benzoyl chloride DMSO: δ 7.0–8.3(m, 9H, arom), 5.82 (s, 2H).

EXAMPLE 69

N-{5-[3-(4-Chloro-phenyl)-[1,2,4]-oxadiazol-5-ylmethoxy)-naphthalen-2-yl}-C,C,C-trifluoro-methanesulfonamide The title compound was prepared from 4-chloro benzoyl chloride DMSO: δ 12.1 broad (s, 1H), 7.1–8.4(m, 10H, arom), 5.8 (s, 2H).

EXAMPLE 70

N-{5-[3-(3',5'-Bistrifluoromethyl-phenyl)-[1,2,4]-oxadiazol-5-ylmethoxy)-naphthalen-2-yl}-C,C,C-trifluoro-methanesulfonamide The title compound was prepared from 3',5'-bistrifluoromethyl benzoyl chloride DMSO: δ 12.1 broad (s, 1H), 7.1–8.6(m, 9H, arom), 5.86 (s, 2H).

EXAMPLE 71

N-{5-[3-(4-Trifluoromethoxy-phenyl)-[1,2,4]-oxadiazol-5-ylmethoxy)-naphthalen-2-yl}-C,C,C-trifluoro-methanesulfonamide The title compound was prepared from 4-triflouromethoxy benzoyl chloride DMSO: δ 11.9 (s, 1H), 7.1–8.3(m, 10H, arom), 5.84 (s, 2H).

EXAMPLE 72

N-{5-[3-(4-Methyl-phenyl)-[1,2,4]-oxa diazol-5-ylmethoxy)-naphthalen-2-yl}-C,C,C-trifluoro-methanesulfonamide The title compound was prepared from 4-methyl benzoyl chloride DMSO: δ 12.0 (s, 1H), 7.1–8.3(m, 10H, arom), 5.8 (s, 2H), 2.36 (s, 3H).

EXAMPLE 73

N-{5-[3-(4-tert-Butyl-phenyl)-[1,2,4]-oxadiazol-5-ylmethoxy)-naphthalen-2-yl}-C,C,C-trifluoro-methanesulfonamide The title compound was prepared from 4-t-butyl benzoyl chloride DMSO: δ 12.1 (s, 1H), 7.1–8.3(m, 10H, arom), 5.8 (s, 2H), 1.3(s, 9H).

EXAMPLE 74

Preparation of [5-(Biphenyl-2-ylmethoxy)-naphthalen-2-yl]-urea

To 100 mg, (0.31 mmol) of the product from Example 27, step 1 in 15 mL of DMF was added 57 mg (0.50 mmol) of trimethylsilyl isocyanate the solution was heated to 50° C. for 1.5 hr. At the end of this time it was poured into 100 mL of water. The resulting precipitate was collected by filtration and taken up in hot ethyl acetate. The excess water was removed by decantation and the solution allow to cool. Hexane was introduced to cloudiness and the solution allow to cool further to yield 55 mg (48%) of product as a colorless solid, m.p. 159–161° C.

$^1$H NMR (400 MHz, DMSO) δ: 8.72 (s, 1H); 7.98 (d, J=2.0 Hz, 1H); 7.92 (d, J=9.2 Hz, 1H); 7.46 (m, 12H); 6.63 (d, J=7.2 Hz, 1H); 5.90 (s, 2H); 5.11 (s, 2H).

Anal. Calcd. for $C_{24}H_{20}N_2O_2$: C, 78.24; H, 5.47; N, 7.60. Found: C, 75.71; H, 5.68; N, 7.70; 368.4388 (+)FAB m/z 369 (M+H), 391 (M+Na).

EXAMPLE 75

[5-(4'-Methoxy-biphenyl-3-ylmethoxy)-naphthalen-2-yl]-urea

The title compound was prepared from the product obtained from Example 20, step 1 using a procedure similar to EXAMPLE 74, m.p. 150 (dec.).

$^1$H NMR (400 MHz, DMSO) δ: 8.74 (s, 1H); 7.49 (m, 14H); 5.92 (s, 2H); 5.32 (s, 2H); 3.79 (s, 3H).

Anal. Calcd. for $C_{25}H_{22}N_2O_3$: C, 75.36; H, 5.57; N, 7.03. Found: C, 71.32; H, 5.64; N, 7.31; 398.4658 (+)ESI m/z 399 (M+H).

EXAMPLE 76

[5-(4'-Chloro-4-methoxy-biphenyl-3-ylmethoxy)-naphthalen-2-yl]-urea

The title compound was prepared from the product obtained from Example 21, step 1 using a procedure similar to EXAMPLE 74, m.p. 200° C. (dec.).

$^1$H NMR (400 MHz, DMSO) δ: 8.72 (s, 1H); 7.46 (m, 13H); 5.91 (s, 2H); 5.26 (s, 2H); 3.88 (s, 3H).

Anal. Calcd. for $C_{25}H_{21}ClN_2O_3$: C, 69.36; H, 4.89; N, 6.47. Found: C, 66.28; H, 4.54; N, 6.14; 432.9108 EI m/z 432.

EXAMPLE 77

[5-(4'-Chloro-biphenyl-4-ylmethoxy)-naphthalen-2-yl]-urea

The title compound was prepared from the product obtained from Example 22, step 1 using a procedure similar to EXAMPLE 74 m.p. 182° C. (dec.).

$^1$H NMR (DMSO) δ: 8.73 (s, 1H); 7.48 (m, 14H); 5.92 (s, 2H); 5.33(s, 2H).

Anal. Calcd. for $C_{24}H_{19}ClN_2O_2$: C, 69.14; H, 5.28; N, 8.28. Found: C, 64.35; H, 4.58; N, 8.18; 402.8848 (+)FAB m/z 403 (M+H).

EXAMPLE 78

N-[5-(Benzothiazol-2-ylmethoxy)-naphthalen-2-yl]-C,C,C-trifluoro-methanesulfonamide 2-amino-5-(Benzothiazol-2-ylmethoxy)-naphthalene Sodium hydride (1.05 g) is added to a cooled solution of 2-Amino-5-naphthol (4.18 g) in dimethylformamide (100 mL). Stir at room temperature 15 minutes and cool mixture. 2-Bromomethylbenzothiazole (6.00 g) is added and mixture to allowed to warm slowly and stir for 24 hours. Remove dimethylformamide in vacuo. Redilute with ethylacetate and absorb onto silica gel. Chromatograph (ethyl acetate/hexane) to give a brown solid (1.20 g, 15%) which was used directly in the next step., m.p. 141–143° C. 1H NMR (DMSO-d$_6$, 400 MHz): d 5.43 (br s, 2H), 5.69 (s, 2H), 6.72 (d, 1H), 6.80 (s, 1H), 6.95 (d, 1H), 7.12–7.20 (m, 2H), 7.45 (t, 1H), 7.54 (t, 1H), 7.97 (d, 1H), 8.02 (d, 1H), 8.14 (d, 1H). MS [EI, m/z]: 306 [M]$^+$. Anal. Calcd. for $C_{18}H_{14}N_2OS$: C, 70.56; H, 4.61; N, 9.14. Found: C, 70.38; H, 4.42; N, 9.25.

N-[5-(Benzothiazol-2-ylmethoxy)-naphthalen-2-yl]-C,C,C-trifluoro-methanesulfonamide 2-amino-5-(Benzothiazol-2-ylmethoxy)-naphthalene (0.77 g) and triethylamine (0.35 mL) dissolved in dichloromethane (75 mL). Cool in an acetone and dry ice bath. Add triflic anhydride (0.42 mL) and allow mixture to warm to room temperature overnight. Partition between water and ethyl acetate. Separate and dry with magnesium sulfate. Concentrate at rotovap to provide the title compound (0.450 g, 40%) as a beige solid, m.p. 190–192° C. 1H NMR (DMSO-d$_6$, 400 MHz): δ 5.82 (s, 2H), 7.17 (d, 1H), 7.46–7.49 (m, 3H), 7.50–7.58 (m, 2H), 7.78 (s, 1H), 8.05 (d, 1H), 8.14 (d, 1H), 8.32 (d, 1H). MS [EI, m/z]: 438 [M]$^+$. Anal. Calcd. for $C_{19}H_{13}F_3N_2O_3S_2$: C, 52.05; H, 2.99; N, 6.39. Found: C, 52.21; H, 3.02; N, 6.15.

EXAMPLE 79

N-[5-(5-methyl-2-phenyl-oxazol-4-ylmethoxy) naphthalen-2-yl]C,C,C-trifluoromethanesulfonamide 5-methyl-2-phenyl-4-Chloromethyloxazole (3.34 g) is added to a chilled mixture of 2-Amino-5-naphthol (2.55 g) and sodium hydride (0.65 g) in dimethylformamide (100 mL). Let stir overnight at room temperature. Concentrate in vacuo. Redilute with ethylacetate and absorb onto silica gel. Chromatograph (ethyl acetate/hexane) to give 2-amino-5-(methyl-2-phenyl-oxazol-4-ylmethoxy)naphthalene (1.59 g, 30%). Without further characterization this amine and triethylamine (0.67 mL) were dissolved in dichloromethane (75 mL). Cooled in an acetone and dry ice bath. Triflic anhydride (0.81 mL) was added and the mixture had warmed to room temperature overnight. Partition between water and ethyl acetate. Separate and dry with magnesium sulfate. Concentrate at rotovap, and triturate with ethyl acetate to provide the title compound (0.70 g, 30%) as a white solid, m.p. 192–194° C. 1H NMR (DMSO-$d_6$, 400 MHz): δ 2.49 (s, 3H), 5.21 (s, 2H), 7.17 (d, 1H), 7.36 (d, 1H), 7.46–755 (m, 5H), 7.73 (s, 1H), 7.93–7.97 (m, 2H), 8.13 (d, 1H). MS [EI, m/z]: 462 [M]$^+$. Anal. Calcd. for $C_{22}H_{17}F_3N_2O_4S$ 0.75($H_2O$): C, 55.52; H, 3.92; N, 5.89. Found: C, 55.62; H, 4.13; N, 5.45.

EXAMPLE 80

N-[5-(2-phenyl-oxazol-4-ylmethoxy)naphthalen-2-yl]C,C,C-trifluoromethanesulfonamide Using same procedure as above 2-phenyl-4-Chloromethyloxazole was coupled with 2-Amino-5-naphthol then reacted with triflic anhydride to provide the title compound (0.630 g, 35%) as a white solid, m.p. 195–197° C. 1H NMR (DMSO-$d_6$, 400 MHz): δ 5.27 (s, 2H), 7.18 (d, 1H), 7.37 (d, 1H), 7.46–7.56 (m, 5H), 7.73 (s, 1H), 7.99–8.02 (d, 2H), 8.21 (d, 1H), 8.43 (s, 1H). MS [EI, m/z]: 449 [M+H]$^+$. Anal. Calcd. for $C_{21}H_{15}F_3N_2O_4$: C, 56.25; H, 3.37; N, 6.25. Found: C, 56.21; H, 3.24; N, 6.22.

EXAMPLE 81

N-[5-[5-methyl-2-(4-trifluoromethylphenyl)-oxazol-4-ylmethoxy]naphthalen-2-yl}C,C,C-trifluoromethanesulfonamide Using same procedure as above 5-methyl-2-(4-trifluoromethylphenyl)-4-Chloromethyloxazole was coupled with 2-Amino-5-naphthol then reacted with triflic anhydride to provide the title compound (0.560 g, 30%) as a white solid, m.p. 212–214° C. 1H NMR (DMSO-$d_6$, 400 MHz): δ 2.52 (s, 3H), 5.24 (s, 2H), 7.17 (d, 1H), 7.35 (d, 1H), 7.47–7.53 (m, 2H), 7.73 (s, 1H), 7.88 (d, 2H), 8.12–8.16 (m, 3H). MS [EI, m/z]: 530 [M]$^+$. Anal. Calcd. for $C_{23}H_{16}F_6N_2O_4S$: C, 52.08; H, 3.04; N, 5.28. Found: C, 52.12; H, 2.91; N, 5.17.

EXAMPLE 82

N-{5-[5-methyl-2-(4-fluoro-phenyl)-oxazol-4-ylmethoxy]naphthalen-2-yl}C,C,C-trifluoromethanesulfonamide Using same procedure as above 5-methyl-2-(4-fluoro-phenyl)-4-Chloromethyloxazole was coupled with 2-Amino-5-naphthol then reacted with triflic anhydride to provide the title compound (0.20 g, 30%) as a white solid, m.p. 178–180° C. 1H NMR (DMSO-$d_6$, 400 MHz): δ 2.48 (s, 3H), 5.20 (s, 2H), 7.16 (d, 1H), 7.33–7.38 (m, 3H), 7.46–7.52 (m, 2H), 7.73 (s, 1H), 7.97–8.02 (m, 2H), 8.13 (d, 1H). MS [EI, m/z]: 481 [M+H]$^+$. Anal. Calcd. for $C_{22}H_{16}F_4N_2O_4S$: C, 55.00; H, 3.36; N, 5.83. Found: C, 56.70; H, 4.27; N, 5.23.

EXAMPLE 83

N-[5-(Naphthalen-2-ylmethoxy)-naphthalen-2-yl]-C,C,C-trifluoro-methanesulfonamide 2-Bromomethylnaphthalene (4.60 g) is added to a mixture of 2-Amino-5-naphthol (3.34 g) and sodium hydride (1.00 g) in dimethylformamide (100 mL) at −40 deg. C. Let stir overnight at room temperature. Concentrate in vacuo. Redilute with ethylacetate and absorb onto silica gel. Chromatograph (ethyl acetate/hexane) to give 2-amino-5-(Naphthalen-2-ylmethoxy)-naphthalene (1.86 g, 30%). Without further characterization this amine and triethylamine (0.90 mL) were dissolved in dichloromethane (75 mL). Cooled in an acetone and dry ice bath. Triflic anhydride (1.05 mL) was added and the mixture had warmed to room temperature overnight. Partition between water and ethyl acetate. Separate and dry with magnesium sulfate. Concentrate at rotovap, and triturate with ethyl acetate to provide the title compound (0.825 g, 30%) as a pale yellow solid, m.p. 140–142° C. 1H NMR (DMSO-$d_6$, 400 MHz): δ 5.47 (s, 2H), 7.12 (d, 1H), 7.40–7.56 (m, 5H), 7.67 (d, 1H), 7.75 (s, 1H), 7.91–7.98 (m, 3H), 8.09 (s, 1H), 8.30 (d, 1H). MS [EI, m/z]: 430 [M−H]$^+$. Anal. Calcd. for $C_{22}H_{16}F_3NO_3S$: C, 61.25; H, 3.74; N, 3.25. Found: C, 61.05; H, 3.81; N, 3.12.

EXAMPLE 84

N-{5-[2-(4-Chloro-phenyl)-oxazol-4-ylmethoxy] naphthalen-2-yl}C,C,C-trifluoromethanesulfonamide Using same procedure as above 2-(4-Chloro-phenyl)-4-Chloromethyloxazole was coupled with 2-Amino-5-naphthol then reacted with triflic anhydride to provide the title compound (0.350 g, 30%) as a white solid, m.p. 198–200° C. 1H NMR (DMSO-$d_6$, 400 MHz): δ 5.28 (s, 2H), 7.20 (d, 1H), 7.40 (d, 1H), 7.47–7.55 (m, 2H), 7.63 (d, 2H), 7.75 (s, 1H), 8.02 (d, 2H), 8.22 (d, 1H), 8.47 (s, 1H). MS [EI, m/z]: 482 [M]$^+$. Anal. Calcd. for $C_{21}H_{14}ClF_3N_2O_4S$: C, 52.24; H, 2.92; N, 5.80. Found: C, 52.45, H, 3.28, N, 5.68.

EXAMPLE 85

N-{5-[2-(4-tert-Butyl-phenyl)-oxazol-4-ylmethoxy] naphthalen-2-yl}C,C,C-trifluoromethanesulfonamide Using same procedure as above 2-(4-tert-Butyl-phenyl)-4-Chloromethyloxazole was coupled with 2-Amino-5-naphthol then reacted with triflic anhydride to provide the title compound (0. 50 g, 30%) as a white solid, m.p. 165–167° C. 1H NMR (DMSO-$d_6$, 400 MHz): δ 1.32 (s, 9H), 5.27 (s, 2H), 7.19 (d, 1H), 7.39 (d, 1H), 7.47–7.54 (m, 2H), 7.56–7.59 (d, 2H), 7.75 (s, 1H), 7.95 (d, 2H), 8.22 (d, 1H), 8.41 (s, 1H). MS [EI, m/z]: 503 [M−H]$^+$. Anal. Calcd. for $C_{25}H_{23}F_3N_2O_4S$: C, 59.52; H, 4.60; N, 5.55. Found: C, 59.23; H, 4.66; N, 5.41.

EXAMPLE 86

N-{5-[2-(4-Bromo-phenyl)-oxazol-4-ylmethoxy] naphthalen-2-yl}C,C,C-trifluoromethanesulfonamide Using same procedure as above 2-(4-Bromo-phenyl)-4-Chloromethyloxazole was coupled with 2-Amino-5- naphthol then reacted with triflic anhydride to provide the title compound (0.25 g, 30%) as a white solid, m.p. 205–207° C. 1H NMR (DMSO-$d_6$, 400 MHz): δ 5.28 (s, 2H), 7.19 (d, 1H), 7.39 (d, 1H), 7.47–7.54 (m, 2H), 7.75 (s, 1H), 7.77 (d, 2H), 7.94 (d, 2H), 8.22 (d, 1H), 8.48 (s, 1H). MS [EI, m/z]: 525 [M−H]$^+$. Anal. Calcd. for $C_{21}H_{14}BrF_3N_2O_4S$: C, 47.83; H, 2.68; N, 5.31. Found: C, 57.66; H, 2.85; N, 5.14.

EXAMPLE 87

N-{5-[2-(4-trifluoromethyl-phenyl)-oxazol-4-ylmethoxy]naphthalen-2-yl}C,C,C-trifluoromethanesulfonamide Using same procedure as above 2-(4-trifluoromethyl-phenyl)-4-Chloromethyloxazole was coupled with 2-Amino-5-naphthol then reacted with triflic anhydride to provide the title compound (0.26 g, 30%) as a white solid, m.p. 205–207° C. 1H NMR (DMSO-$d_6$, 400 MHz): δ 5.31 (s, 2H), 7.19 (d, 1H), 7.39 (d, 1H), 7.47–7.54 (m, 2H), 7.74 (s, 1H), 7.93 (d, 2H), 8.22 (d, 2H), 8.24 (s, 1H), 8.55 (s, 1H). MS [EI, m/z]: 516 [M]$^+$. Anal. Calcd. for $C_{22}H_{14}F_6N_2O_4S$ 0.5($H_2O$): C, 50.25; H, 2.88; N, 5.33. Found: C, 50.39; H, 2.90; N, 5.25.

EXAMPLE 88

N-[5-[2-o-tolyl-oxazol-4-ylmethoxy)naphthalen-2-yl]C,C,C-trifluoromethanesulfonamide Using same procedure as above 2-o-tolyl-4-Chloromethyloxazole was coupled with 2-Amino-5-naphthol then reacted with triflic anhydride to provide the title compound (0.06 g, 30%) as a pale yellow solid, m.p. 127–130° C. 1H NMR (DMSO-$d_6$, 400 MHz): d 2.65 (s, 3H), 5.30 (s, 2H), 7.23 (d, 1H), 7.34–7.45 (m, 4H), 7.47–7.55 (m, 2H), 7.75 (s, 1H), 7.95 (d, 2H), 8.24 (d, 1H), 8.45 (s, 1H). MS [EI, m/z]: 461 [M−H]$^+$. Anal. Calcd. for $C_{22}H_{17}F_3N_2O_4S$: C, 57.14; H, 3.71; N, 6.06. Found: C, 58.08; H, 3.81; N, 6.01.

What is claimed is:

1. A compound of formula (I) having the structure

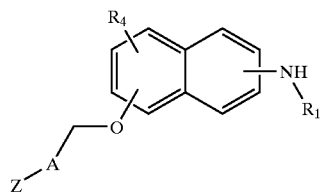

(I)

wherein:

Z is

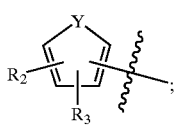

Y is C=C;

$R_1$ is selected from —$SO_2CF_3$, —$SO_2Ar$, —$SO_2CH_3$, —$SO_2CH_2CF_3$, —$CONH_2$, —$CSNHCH_3$, —CONHAr, —COAr, —$COCCl_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —$NO_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

$R_2$ and $R_3$ are independently selected from hydrogen, halogen, hydroxy, -alkoxy of 1–6 carbon atoms, —$CF_3$, —CN, alkyl of 1–6 carbon atoms, or —CH=CHPh; or $R_2$ and $R_3$ may be taken together as —C($CH_3$)$_2$$CH_2CH_2$—C($CH_3$)$_2$—, or —$OCH_2CH_2O$—; or $R_2$ and $R_3$ may be taken together as —CH=CH—CH=CH—, when A is not a bond;

$R_4$ is hydrogen or halogen,

A is

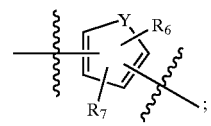

wherein $R_6$, and $R_7$ are each, independently, hydrogen, halo, hydroxy, alkoxy of 1–6 carbon atoms, $CF_3$, CN, or alkyl of 1–6 carbon atoms;

or a pharmaceutically acceptable salt form thereof.

2. The compound of claim 1, having the structure of formula (II):

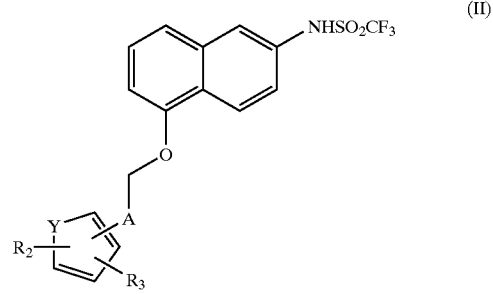

(II)

wherein,

A is

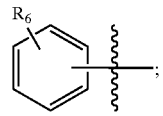

Y is —C=C—;

or a pharmaceutically acceptable salt form thereof.

3. The compound of claim 1, having the structure of formula (III):

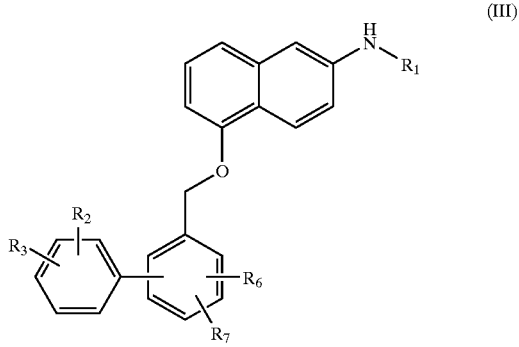

(III)

or a pharmaceutically acceptable salt form thereof.

4. The compound of claim 1, which is
   a) C,C,C-Trifluoro-N-[5-biphenyl-3-ylmethoxy)-naphthalen-2-yl]-methanesulfonamide;
   b) N-[5-(3',4'-Dichloro-3-fluoro-biphenyl-4-ylmethoxy)-naphthalen-2-yl]-C,C,C-trifluoro-methanesulfonamide;
   c) N-[5-(4-naphthalen-2-yl-benzyloxy-3-ylmethoxy)-naphthalen-2-yl]-C,C,C-trifluoro-methanesulfonamide;
   d) C,C,C-Trifluoro-N-[5-(3-fluoro-4'-trifluoromethyl-biphenyl-4-ylmethoxy)-naphthalen-2-yl]-methanesulfonamide;
   e) N-[5-(4'-tert-Butyl-3-fluoro-biphenyl-4-ylmethoxy)-naphthalen-2-yl]-C,C,C-trifluoro-methanesulfonamide;
   f) N-[5-(3,4'-Dichloro-biphenyl-4-ylmethoxy)-naphthalen-2-yl]-C,C,C-trifluoro-methanesulfonamide;
   g) C,C,C-Trifluoro-N-[5-(3,3',4'-trichloro-biphenyl-4-ylmethoxy)-naphthalen-2-yl]-methanesulfonamide; or
   h) C,C,C-Trifluoro-N-[5-(3-fluoro-biphenyl-4-ylmethoxy)-naphthalen-2-yl]-methanesulfonamide;

or a pharmaceutically acceptable salt thereof.

5. A method of lowering glucose levels in a mammal in need thereof which comprises providing to said mammal, a compound of formula (I) having the structure

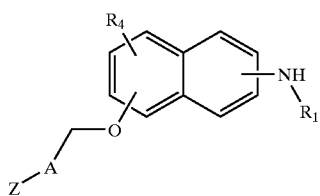

(I)

wherein:
Z is

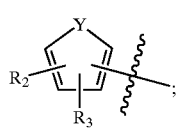

Y is C=C;

$R_1$ is selected from —SO$_2$CF$_3$, —SO$_2$Ar, —SO$_2$CH$_3$, —SO$_2$CH$_2$CF$_3$, —CONH$_2$, —CSNHCH$_3$, —CONHAr, —COAr, —COCCl$_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —NO$_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

$R_2$ and $R_3$ are independently selected from hydrogen, halogen, hydroxy, -alkoxy of 1–6 carbon atoms, —CF$_3$, —CN, alkyl of 1–6 carbon atoms, or —CH=CHPh; or $R_2$ and $R_3$ may be taken together as —C(CH$_3$)$_2$CH$_2$CH$_2$—C(CH$_3$)$_2$—, or —OCH$_2$CH$_2$O—; or $R_2$ and $R_3$ may be taken together as —CH=CH—CH=CH—, when A is not a bond;

$R_4$ is hydrogen or halogen,

A is

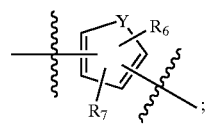

wherein $R_6$, and $R_7$ are each, independently, hydrogen, halo, hydroxy, alkoxy of 1–6 carbon atoms, CF$_3$, CN, or alkyl of 1–6 carbon atoms;

or a pharmaceutically acceptable salt form thereof.

6. A method of treating type II diabetes in a mammal in need thereof which comprises providing to said mammal, a compound of formula (I) having the structure

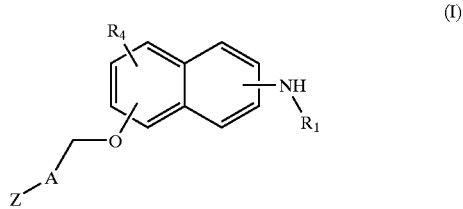

(I)

wherein:
Z is

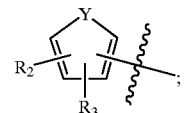

Y is C=C;

$R_1$ is selected from —SO$_2$CF$_3$, —SO$_2$Ar, —SO$_2$CH$_3$, —SO$_2$CH$_2$CF$_3$, —CONH$_2$, —CSNHCH$_3$, —CONHAr, —COAr, —COCCl$_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —NO$_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

$R_2$ and $R_3$ are independently selected from hydrogen, halogen, hydroxy, -alkoxy of 1–6 carbon atoms, —$CF_3$, —CN, alkyl of 1–6 carbon atoms, or —CH=CHPh; or $R_2$ and $R_3$ may be taken together as —C(CH$_3$)$_2$CH$_2$CH$_2$—C(CH$_3$)$_2$—, or —OCH$_2$CH$_2$O—; or $R_2$ and $R_3$ may be taken together as —CH=CH—CH=CH—, when A is not a bond;

$R_4$ is hydrogen or halogen,

A is

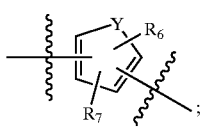

wherein $R_6$, and $R_7$ are each, independently, hydrogen, halo, hydroxy, alkoxy of 1–6 carbon atoms, $CF_3$, CN, or alkyl of 1–6 carbon atoms;

or a pharmaceutically acceptable salt form thereof.

7. A method of treating primary hypertension in a mammal in need thereof, which comprises providing to said mammal a compound of formula (I) having the structure

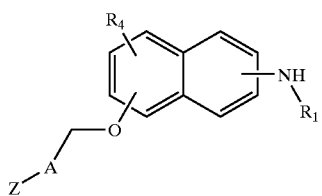

wherein:

Z is

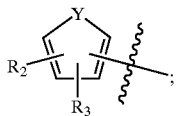

Y is C=C;

$R_1$ is selected from —SO$_2$CF$_3$, —SO$_2$Ar, —SO$_2$CH$_3$, —SO$_2$CH$_2$CF$_3$, —CONH$_2$, —CSNHCH$_3$, —CONHAr, —COAr, —COCCl$_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —NO$_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

$R_2$ and $R_3$ are independently selected from hydrogen, halogen, hydroxy, -alkoxy of 1–6 carbon atoms, —$CF_3$, —CN, alkyl of 1–6 carbon atoms, or —CH=CHPh; or $R_2$ and $R_3$ may be taken together as —C(CH$_3$)$_2$CH$_2$CH$_2$—C(CH$_3$)$_2$—, or —OCH$_2$CH$_2$O—; or $R_2$ and $R_3$ may be taken together as —CH=CH—CH=CH—, when A is not a bond;

$R_4$ is hydrogen or halogen,

A is

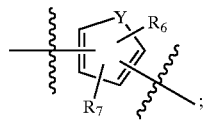

wherein $R_6$, and $R_7$ are each, independently, hydrogen, halo, hydroxy, alkoxy of 1–6 carbon atoms, $CF_3$, CN, or alkyl of 1–6 carbon atoms;

or a pharmaceutically acceptable salt form thereof; wherein the primary hypertension is associated with the occurrence of insulin resistance or type II diabetes in the mammal.

8. A method of treating atherosclerosis in a mammal in need thereof, which comprises providing to said mammal a compound of formula (I) having the structure

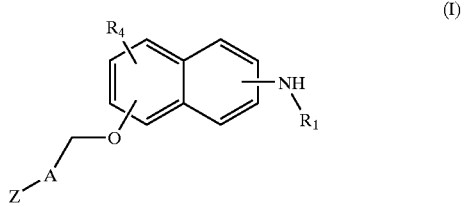

wherein:

Z is

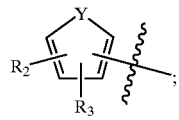

Y is C=C;

$R_1$ is selected from —SO$_2$CF$_3$, —SO$_2$Ar, —SO$_2$CH$_3$, —SO$_2$CH$_2$CF$_3$, —CONH$_2$, —CSNHCH$_3$, —CONHAr, —COAr, —COCCl$_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —NO$_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

$R_2$ and $R_3$ are independently selected from hydrogen, halogen, hydroxy, -alkoxy of 1–6 carbon atoms, —$CF_3$, —CN, alkyl of 1–6 carbon atoms, or —CH=CHPh; or $R_2$ and $R_3$ may be taken together as —C(CH$_3$)$_2$CH$_2$CH$_2$—C(CH$_3$)$_2$—, or —OCH$_2$CH$_2$O—; or $R_2$ and $R_3$ may be taken together as —CH=CH—CH=CH—, when A is not a bond;

$R_4$ is hydrogen or halogen,

A is

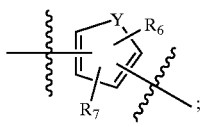

wherein $R_6$, and $R_7$ are each, independently, hydrogen, halo, hydroxy, alkoxy of 1–6 carbon atoms, $CF_3$, $CN$, or alkyl of 1–6 carbon atoms;

or a pharmaceutically acceptable salt form thereof; wherein the atherosclerosis is associated with the occurrence of insulin resistance or type II diabetes in the mammal.

9. A pharmaceutical composition which comprises a compound of formula (I) having the structure

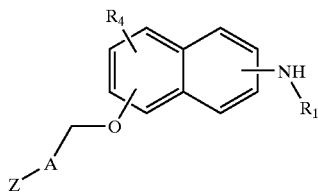

(I)

wherein:

Z is

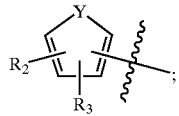

Y is C=C;

$R_1$ is selected from —$SO_2CF_3$, —$SO_2Ar$, —$SO_2CH_3$, —$SO_2CH_2CF_3$, —$CONH_2$, —$CSNHCH_3$, —$CONHAr$, —$COAr$, —$COCCl_3$;

Ar is phenyl, naphthyl, pyridyl, or quinolyl, which may be optionally mono- or di-substituted with alkyl of 1–6 carbon atoms, alkenyl of 2–7 carbon atoms, halogen, hydroxyl, alkoxy of 1–6 carbon atoms, —CN, —$NO_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl;

$R_2$ and $R_3$ are independently selected from hydrogen, halogen, hydroxy, -alkoxy of 1–6 carbon atoms, —$CF_3$, —CN, alkyl of 1–6 carbon atoms, or —CH=CHPh; or $R_2$ and $R_3$ may be taken together as —$C(CH_3)_2CH_2CH_2$—$C(CH_3)_2$—, or —$OCH_2CH_2O$—; or $R_2$ and $R_3$ may be taken together as —CH=CH—CH=CH—, when A is not a bond;

$R_4$ is hydrogen or halogen,

A is

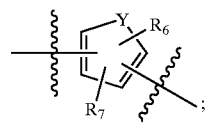

wherein $R_6$, and $R_7$ are each, independently, hydrogen, halo, hydroxy, alkoxy of 1–6 carbon atoms, $CF_3$, $CN$, or alkyl of 1–6 carbon atoms;

or a pharmaceutically acceptable salt form thereof, and a pharmaceutical carrier.

10. The method of claim 5, wherein the compound has the structure of formula (II):

(II)

wherein,
A is

Y is —C=C—;
or a pharmaceutically acceptable salt form thereof.

11. The method of claim 5, wherein the compound has the structure of formula (III):

(III)

or a pharmaceutically acceptable salt form thereof.

12. The method of claim 5, wherein the compound is:

a) C,C,C-Trifluoro-N-[5-biphenyl-3-ylmethoxy)-naphthalen-2-yl]-methanesulfonamide;

b) N-[5-(3',4'-Dichloro-3-fluoro-biphenyl-4-ylmethoxy)-naphthalen-2-yl]-C,C,C-trifluoro-methanesulfonamide;

c) N-[5-(4-naphthalen-2-yl-benzyloxy-3-ylmethoxy)-naphthalen-2-yl]-C,C,C-trifluoro-methanesulfonamide;

d) C,C,C-Trifluoro-N-[5-(3-fluoro-4'-trifluoromethyl-biphenyl-4-ylmethoxy)-naphthalen-2-yl]-methanesulfonamide;
e) N-[5-(4'-tert-Butyl-3-fluoro-biphenyl-4-ylmethoxy)-naphthalen-2-yl]-C,C,C-trifluoro-methanesulfonamide;
f) N-[5-(3,4'-Dichloro-biphenyl-4-ylmethoxy)-naphthalen-2-yl]-C,C,C-trifluoro-methanesulfonamide;
g) C,C,C-Trifluoro-N-[5-(3,3',4'-trichloro-biphenyl-4-ylmethoxy)-naphthalen-2-yl]-methanesulfonamide; or
h) C,C,C-Trifluoro-N-[5-(3-fluoro-biphenyl-4-ylmethoxy)-naphthalen-2-yl]-methanesulfonamide;

or a pharmaceutically acceptable salt thereof.

13. The method of claim 6, wherein the compound has the structure of formula (II):

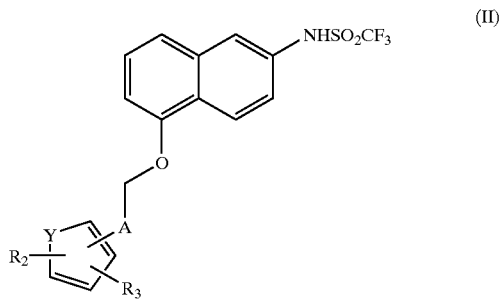

(II)

wherein,
A is

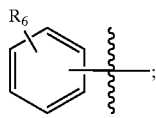

;

Y is —C═C—;
or a pharmaceutically acceptable salt form thereof.

14. The method of claim 6, wherein the compound has the structure of formula (III):

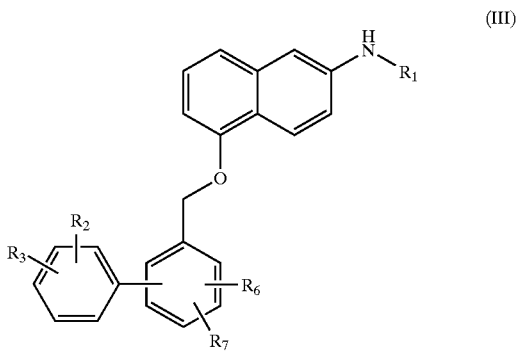

(III)

or a pharmaceutically acceptable salt form thereof.

15. The method of claim 6, wherein the compound is:
a) C,C,C-Trifluoro-N-[5-biphenyl-3-ylmethoxy)-naphthalen-2-yl]-methanesulfonamide;
b) N-[5-(3',4'-Dichloro-3-fluoro-biphenyl-4-ylmethoxy)-naphthalen-2-yl]-C,C,C-trifluoro-methanesulfonamide;
c) N-[5-(4-naphthalen-2-yl-benzyloxy-3-ylmethoxy)-naphthalen-2-yl]-C,C,C-trifluoro-methanesulfonamide;

d) C,C,C-Trifluoro-N-[5-(3-fluoro-4'-trifluoromethyl-biphenyl-4-ylmethoxy)-naphthalen-2-yl]-methanesulfonamide;
e) N-[5-(4'-tert-Butyl-3-fluoro-biphenyl-4-ylmethoxy)-naphthalen-2-yl]-C,C,C-trifluoro-methanesulfonamide;
f) N-[5-(3,4'-Dichloro-biphenyl-4-ylmethoxy)-naphthalen-2-yl]-C,C,C-trifluoro-methanesulfonamide;
g) C,C,C-Trifluoro-N-[5-(3,3',4'-trichloro-biphenyl-4-ylmethoxy)-naphthalen-2-yl]-methanesulfonamide; or
h) C,C,C-Trifluoro-N-[5-(3-fluoro-biphenyl-4-ylmethoxy)-naphthalen-2-yl]-methanesulfonamide;

or a pharmaceutically acceptable salt thereof.

16. The method of claim 7, wherein the compound has the structure of formula (II):

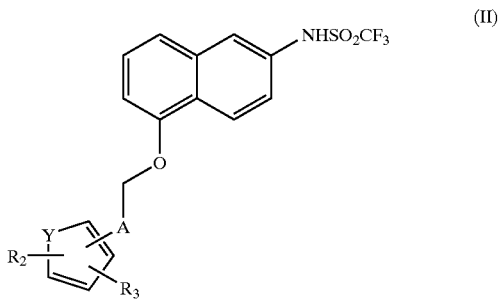

(II)

wherein,
A is

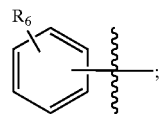

;

Y is —C═C—;
or a pharmaceutically acceptable salt form thereof.

17. The method of claim 7, wherein the compound has the structure of formula (III):

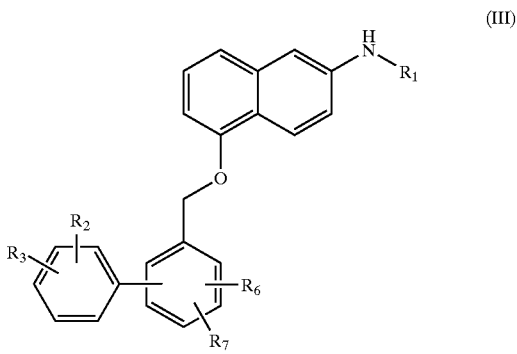

(III)

or a pharmaceutically acceptable salt form thereof.

18. The method of claim 7, wherein the compound is:
a) C,C,C-Trifluoro-N-[5-biphenyl-3-ylmethoxy)-naphthalen-2-yl]-methanesulfonamide;
b) N-[5-(3',4'-Dichloro-3-fluoro-biphenyl-4-ylmethoxy)-naphthalen-2-yl]-C,C,C-trifluoro-methanesulfonamide;
c) N-[5-(4-naphthalen-2-yl-benzyloxy-3-ylmethoxy)-naphthalen-2-yl]-C,C,C-trifluoro-methanesulfonamide;

d) C,C,C-Trifluoro-N-[5-(3-fluoro-4'-trifluoromethyl-biphenyl-4-ylmethoxy)-naphthalen-2-yl]-methanesulfonamide;
e) N-[5-(4'-tert-Butyl-3-fluoro-biphenyl-4-ylmethoxy)-naphthalen-2-yl]-C,C,C-trifluoro-methanesulfonamide;
f) N-[5-(3,4'-Dichloro-biphenyl-4-ylmethoxy)-naphthalen-2-yl]-C,C,C-trifluoro-methanesulfonamide;
g) C,C,C-Trifluoro-N-[5-(3,3',4'-trichloro-biphenyl-4-ylmethoxy)-naphthalen-2-yl]-methanesulfonamide; or
h) C,C,C-Trifluoro-N-[5-(3-fluoro-biphenyl-4-ylmethoxy)-naphthalen-2-yl]-methanesulfonamide;

or a pharmaceutically acceptable salt thereof.

19. The method of claim 8, wherein the compound has the structure of formula (II):

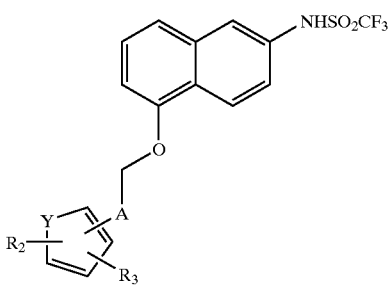

wherein,

A is

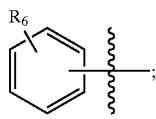

Y is —C≡C—;

or a pharmaceutically acceptable salt form thereof.

20. The method of claim 8, wherein the compound has the structure of formula (III):

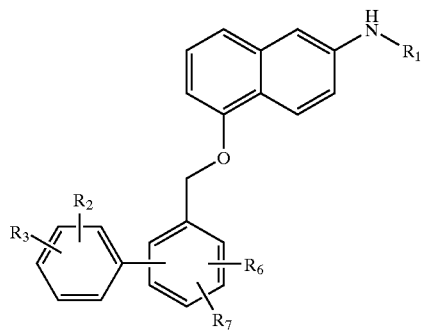

or a pharmaceutically acceptable salt form thereof.

21. The method of claim 8, wherein the compound is:

a) C,C,C-Trifluoro-N-[5-biphenyl-3-ylmethoxy)-naphthalen-2-yl]-methanesulfonamide;
b) N-[5-(3',4'-Dichloro-3-fluoro-biphenyl-4-ylmethoxy)-naphthalen-2-yl]-C,C,C-trifluoro-methanesulfonamide;
c) N-[5-(4-naphthalen-2-yl-benzyloxy-3-ylmethoxy)-naphthalen-2-yl]-C,C,C-trifluoro-methanesulfonamide;
d) C,C,C-Trifluoro-N-[5-(3-fluoro-4'-trifluoromethyl-biphenyl-4-ylmethoxy)-naphthalen-2-yl]-methanesulfonamide;
e) N-[5-(4'-tert-Butyl-3-fluoro-biphenyl-4-ylmethoxy)-naphthalen-2-yl]-C,C,C-trifluoro-methanesulfonamide;
f) N-[5-(3,4'-Dichloro-biphenyl-4-ylmethoxy)-naphthalen-2-yl]-C,C,C-trifluoro-methanesulfonamide;
g) C,C,C-Trifluoro-N-[5-(3,3',4'-trichloro-biphenyl-4-ylmethoxy)-naphthalen-2-yl]-methanesulfonamide; or
h) C,C,C-Trifluoro-N-[5-(3-fluoro-biphenyl-4-ylmethoxy)-naphthalen-2-yl]-methanesulfonamide;

or a pharmaceutically acceptable salt thereof.

* * * * *